US006879936B2

(12) United States Patent
Dilger

(10) Patent No.: US 6,879,936 B2
(45) Date of Patent: Apr. 12, 2005

(54) DIAGNOSTIC APPARATUS AND METHODS FOR A CHEMICAL DETECTION SYSTEM

(75) Inventor: John P. Dilger, Marshalltown, IA (US)

(73) Assignee: Fisher Controls International LLC, St. Louis, MO (US)

( * ) Notice: Subject to any disclaimer, the term of this patent is extended or adjusted under 35 U.S.C. 154(b) by 379 days.

(21) Appl. No.: 10/042,979

(22) Filed: Jan. 9, 2002

(65) Prior Publication Data

US 2003/0127340 A1 Jul. 10, 2003

(51) Int. Cl.⁷ .............................................. G01N 1/00
(52) U.S. Cl. ........................ 702/183; 702/22; 702/23; 702/30; 702/31; 702/32; 702/104; 702/127
(58) Field of Search ........................ 702/22–27, 30–32, 702/50, 51, 85, 90, 91, 104, 127–129, 183, 185; 73/23.31, 169; 340/632, 634, 605; 700/272; 422/58; 205/775

(56) References Cited

U.S. PATENT DOCUMENTS

| | | | | |
|---|---|---|---|---|
| 4,461,167 A | * | 7/1984 | Kent et al. .................. 73/29.02 |
| 4,627,269 A | * | 12/1986 | Forster et al. .............. 73/31.06 |
| 4,703,646 A | * | 11/1987 | Muller et al. .............. 73/24.01 |
| 4,726,225 A | * | 2/1988 | Brace et al. ............. 73/204.23 |
| 5,410,495 A | * | 4/1995 | Ramamurthi ................ 702/100 |
| 5,451,923 A | | 9/1995 | Seberger et al. ....... 340/310.06 |
| 5,487,312 A | | 1/1996 | Kahl et al. ............... 73/863.01 |
| 5,541,851 A | * | 7/1996 | Sato et al. .................. 700/266 |
| 5,569,838 A | * | 10/1996 | Broedel et al. ............ 73/23.31 |
| 5,733,436 A | * | 3/1998 | Demisch et al. ............ 205/775 |
| 5,814,524 A | * | 9/1998 | Walt et al. .................. 436/518 |
| 6,029,506 A | * | 2/2000 | Dilger ........................ 73/46 |
| 6,174,289 B1 | | 1/2001 | Binder ....................... 600/532 |
| 6,200,443 B1 | | 3/2001 | Shen et al. ................. 204/401 |
| 6,222,366 B1 | | 4/2001 | Dilger ........................ 324/319 |
| 6,272,938 B1 | * | 8/2001 | Baghel et al. ............ 73/863.23 |
| 6,300,638 B1 | * | 10/2001 | Groger et al. ............ 250/458.1 |
| 6,345,234 B1 | * | 2/2002 | Dilger et al. ................ 702/24 |
| 6,455,319 B1 | * | 9/2002 | Lewis et al. ................ 436/151 |
| 6,532,793 B1 | * | 3/2003 | Palocz-Andresen ........ 73/23.31 |
| 6,539,311 B1 | * | 3/2003 | Berger ........................ 702/23 |
| 6,647,343 B1 | * | 11/2003 | Guthrie et al. .............. 702/30 |
| 2003/0052083 A1 | * | 3/2003 | Kim et al. .................... 216/59 |

FOREIGN PATENT DOCUMENTS

| GB | 841563 a | * 5/1998 |
|---|---|---|
| WO | WO 99/12471 | 3/1999 |
| WO | WO 00/67634 | 11/2000 |

OTHER PUBLICATIONS

International Preliminary Examination Report for PCT/US02/36924, mailed Apr. 14, 2004.
Written Opinion for PCT/US02/36924, mailed Dec. 8, 2003.
International Search Report for PCT/US02/36924, issued Apr. 16, 2003.

* cited by examiner

*Primary Examiner*—Carol S Tsai
(74) *Attorney, Agent, or Firm*—Marshall, Gerstein & Borun LLP

(57) ABSTRACT

A chemical detection system performs controlled exposures to diagnose the pneumatic components and chemical sensors prior to measuring a chemical emission. A control module provides the system control and data processing to perform the diagnosis. The control module manipulates an emission sample retrieval system to provide precise exposure during the diagnostic routines. A sensor interface circuit interrogates the chemical sensors and stores the data for analysis. The chemical sensor exhibits predictable changes in response during predetermined exposure scenarios. By utilizing numerous time domain signal processing techniques, both system and sensor level fault conditions are determined.

17 Claims, 14 Drawing Sheets

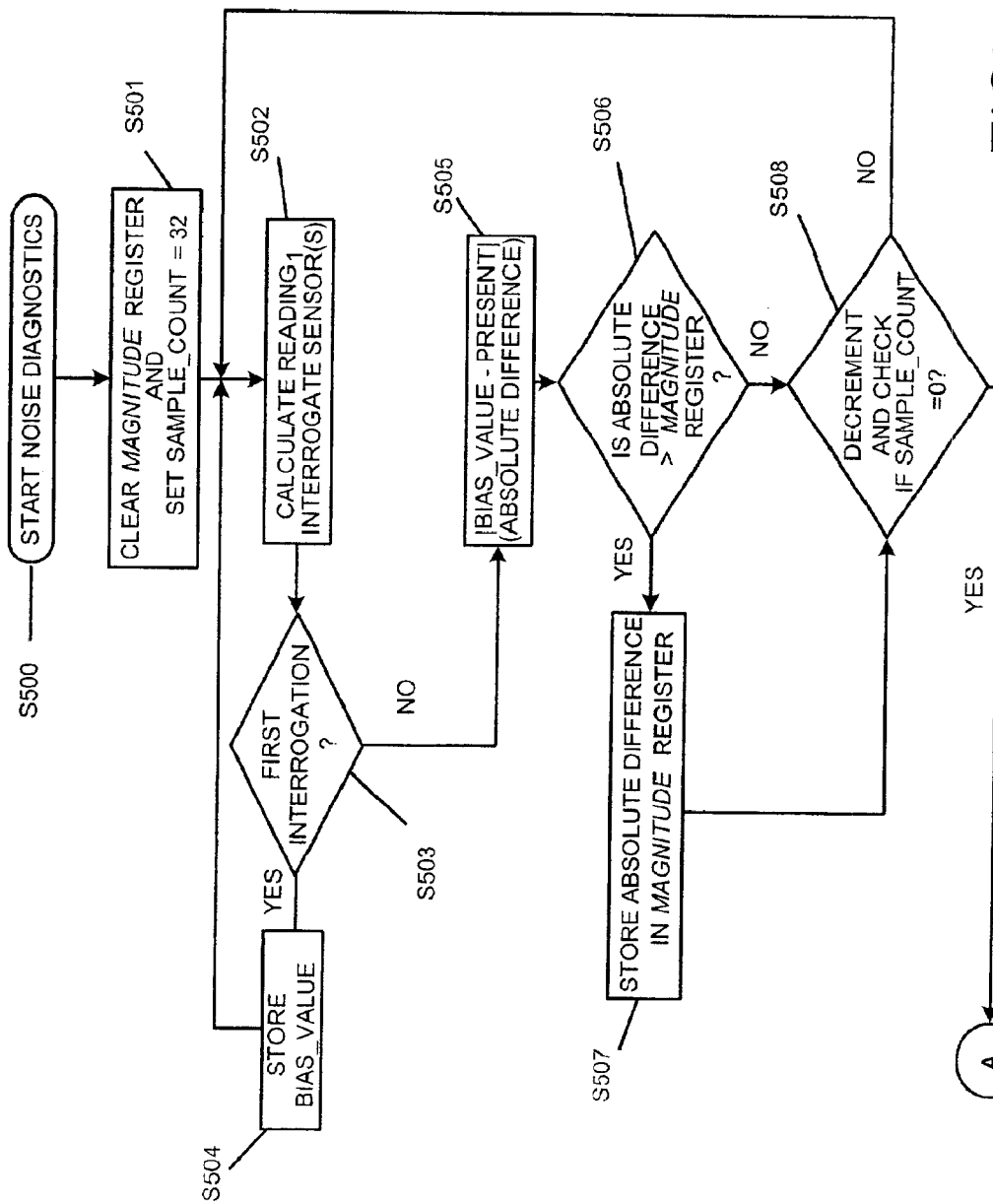

DIAGNOSTIC APPARATUS AND METHODS FOR A CHEMICAL DETECTION SYSTEM

CROSS-REFERENCE TO RELATED U.S. PATENT(S)

This application is related to U.S. Pat. No. 6,222,366, filed on May 10, 1999, entitled "High Frequency Measuring Circuit with Inherent Noise Reduction for Resonating Chemical Sensors", U.S. Pat. No. 6,029,506, filed on Nov. 12, 1997, entitled "Sample Retrieval System", and U.S. Pat. No. 5,451,923, filed on Sep. 2, 1994, entitled "Communication System and Method", and is assigned to the same assignee as the present patent application, and is hereby incorporated by reference.

FIELD OF THE INVENTION

This invention relates to an apparatus and method for diagnosing a chemical detection system used for quantifying volatile organic emissions from equipment used in the process industry.

BACKGROUND

Industrial plants that handle volatile organic compounds (VOCs) typically experience unwanted emissions of those compounds into the atmosphere from point sources such as smokestacks and non-point sources such as valves, pumps, and vessels containing the VOCs. Emissions from non-point sources typically occur due to leakage of the VOCs from joints and seals and are referred to as "fugitive emissions". Fugitive emissions from control valves typically occur as leakage through the packing set around the valve stem. Control valves used in demanding service conditions involving large temperature fluctuations and frequent movements of the valve stem commonly suffer accelerated deterioration of the valve stem packing set.

The United States Environmental Protection Agency (EPA) has promulgated regulations specifying maximum permitted leakage of certain hazardous air pollutants from control valves (e.g. Benzene, Toluene, 1,1,1-Trichloroethane). The regulations require facility operators to perform periodic surveys of the emissions from all control valves and pump seals. The survey interval frequency may be monthly, quarterly, semiannual, or annual. If the facility operator can document that a certain percentage of valves and pumps with excessive leakage are below a prescribed minimum, the required surveys become less frequent. Thus, achieving a low percentage of leaking valves reduces the number of surveys required per year, which may result in large cost savings.

By installing automated chemical detection systems onto devices subject to the most demanding service, leaking devices can be identified and repaired so that compliance with the EPA regulations can be more readily achieved. More importantly, installing accurate chemical detection systems provides an early warning system, one that can alert the facility operator to a potential device failure and enable preventive measures to be taken before excessive leakage occurs.

To successfully achieve the goal of deploying an automated chemical detection system in an industrial environment, the chemical detection system must contain a component that efficiently collects fugitive emissions emanating from a piece of equipment and transport the emission to a gas sensor array. This component of the chemical detection system is called the sample retrieval system. The sample retrieval system must deliver the sample stream at a known flow rate in order to permit the gas sensors to make accurate and consistent measurements of the concentration of the fugitive emission.

Employing gas sensors in an industrial environment requires designing sensors that perform satisfactorily in the presence of high relative humidity (up to 85%) through a broad temperature range (from −10 C. to +50 Celsius). The sensors must be able to discriminate between the emissions of interest and other environmental contaminants, while retaining sufficient sensitivity to detect low concentrations of the fugitive emissions. The sensors must also be able to operate in other harsh environments including areas subject to spray washing and high vibration.

Consequently, the design of a field deployed chemical detection system requires both a unique physical design and the ability to self-diagnosis fault conditions to ensure proper operation prior to reporting a leak. Numerous fault conditions may result in erroneous readings. For example, variations in flow can change the thermodynamics of chemical sensing and induce errors. Permanent shifts in sensor baseline frequency can result from undesired chemical exposures, particulate accumulation, and temperature and humidity extremes. Furthermore, certain species of chemical sensors will suffer irreversible change when exposure levels exceed their saturation limit. These fault conditions can produce measurement errors or "false positive" leak reports. Responding to false positive leak reports could be as costly as performing the manual surveys.

Numerous diagnostic methods have been previously proposed. One such method, described in U.S. Pat. No. 6,200,443 B1, requires an external stimulus containing a surrogate emission to excite the Carbon Monoxide sensors. Based upon the expected system and sensor response to the surrogate, a fault determination is made. This method is disadvantageous due to the required storage and maintenance of surrogate compounds within the measurement system. Thus, the present invention addresses the concerns set forth above.

SUMMARY

Accordingly, it is the object of this invention to provide an apparatus and methods for performing diagnostic routines in a chemical detection system to determine fault conditions without the use of a surrogate compound.

One aspect of the invention provides an apparatus for detecting fault conditions relating to sample flow failure, erratic readings due to sensor noise, and limiting sensor damage due to excessive emission exposure.

Another aspect of the invention provides a method to detect valve failures or system port obstructions by analyzing chemical sensor response to controlled sample flow during diagnostic routines.

Another aspect of the present invention teaches how to determine the absolute drift of sensor baseline frequencies.

Yet another aspect of the present invention provides a method for the detection and quantification of both chemical sensor and chemical detection system noise.

In yet another aspect, the present invention teaches a method to detect excessive fugitive emission presence to prevent chemical sensor damage.

BRIEF DESCRIPTION OF THE DRAWINGS

The features and advantages of the present invention will be best appreciated upon reference to the following detailed description and the accompanying drawings, in which:

FIGS. 5A and 5B are flow charts showing the implementation of a sensor noise diagnostic routine for QCMs.

DETAILED DESCRIPTION

For any chemical detection system to perform adequately, numerous design techniques must be utilized. For example, a system designed to present the chemical sensors with the chemical species of interest must be fully functional prior to initiating a measurement scenario. Additionally, the chemical sensors must be designed to withstand contaminating elements within the operational environment. The present invention not only teaches those skilled in the art how to validate system operation, but also how to confirm the health and integrity of the chemical sensors themselves.

To fully appreciate the advantages of the present invention, it is necessary to have an understanding of the systems' components and how they operate to detect chemicals. Although the preferred embodiment teaches diagnostic techniques related to control valves, those skilled in the art will recognize the applicability to other process equipment such as pumps. Turning to the drawings and referring initially to FIG. 1A, a block diagram of an illustrative embodiment of the invention is given, showing the major components of the chemical detection system.

Large and complex process plants create the consumer goods used throughout the world. Consumer goods ranging from food products to crude oil are processed in these large industrial facilities which rely on computer systems to control their processes. The computer system referenced as a process control system 40 in FIG. 1A communicates with many different types of process control devices and instrumentation. In the present invention, the process control system 40 communicates with a control valve, hereafter referred to as an emission source 12. These communications may require the emission source 12 to move its valve stem in accordance with control strategy implemented by the process control computer 40 and are communicated through a communication protocol 17 as described in U.S. Pat. No. 5,451,923 and is assigned to Fisher Controls International Inc. and hereby incorporated by reference. As previously described, these harsh operating conditions expedite the degradation of the packing set around the valve stem of the emission source 12 and fugitive emissions or leaks will occur.

Figure 1A:
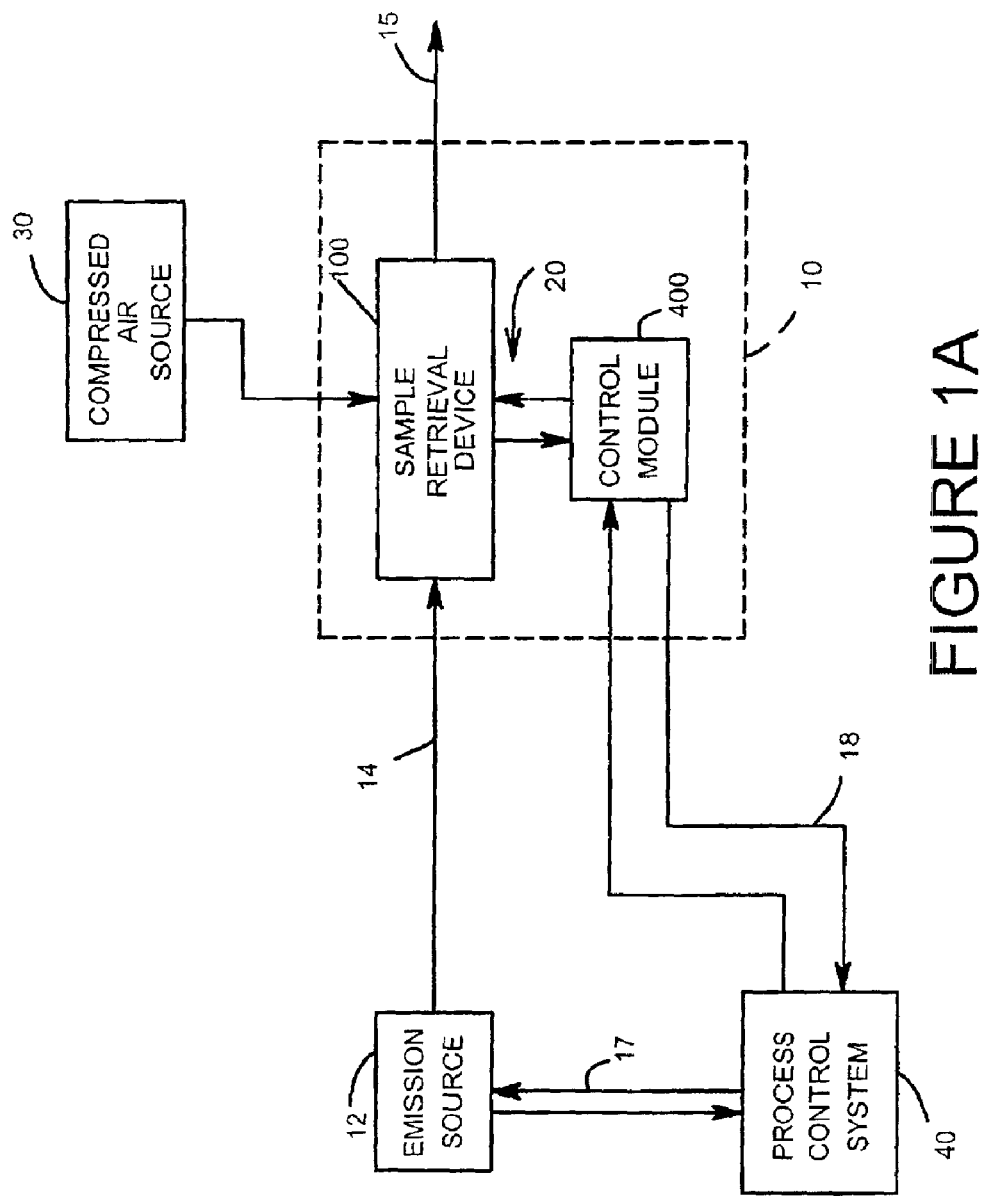
FIG. 1A is a block diagram showing the major components of a chemical detection system.

A chemical detection system 10 is designed to detect extremely small concentrations from the emission source 12. Detection limits of ten parts per million are common. In these extremely small concentrations, the emissions are generally in gas phase. FIG. 1A depicts emission source 12 producing a leak in emission sample stream 14 and collected by a sample retrieval system 100. A novel sample retrieval system 100 is described in U.S. Pat. No. 6,029,506 and is assigned to Fisher Controls International, Inc. and hereby incorporated by reference.

Process control facilities make wide use of compressed air to operate control valves. This abundant energy source provides the chemical detection system 10 with the facilities to collect the emissions in emission sample stream 14. A compressed air source 30 provides the motive force to evacuate the sample retrieval system 100 to draw the emission into the chemical detection system 10. A control module 400 provides the actuation and timing logic for the sample retrieval system 100 through an electrical interface 20. Upon completion of a diagnostic and measurement scenario, sample contents 15 are expelled from the system.

Figure 1B:
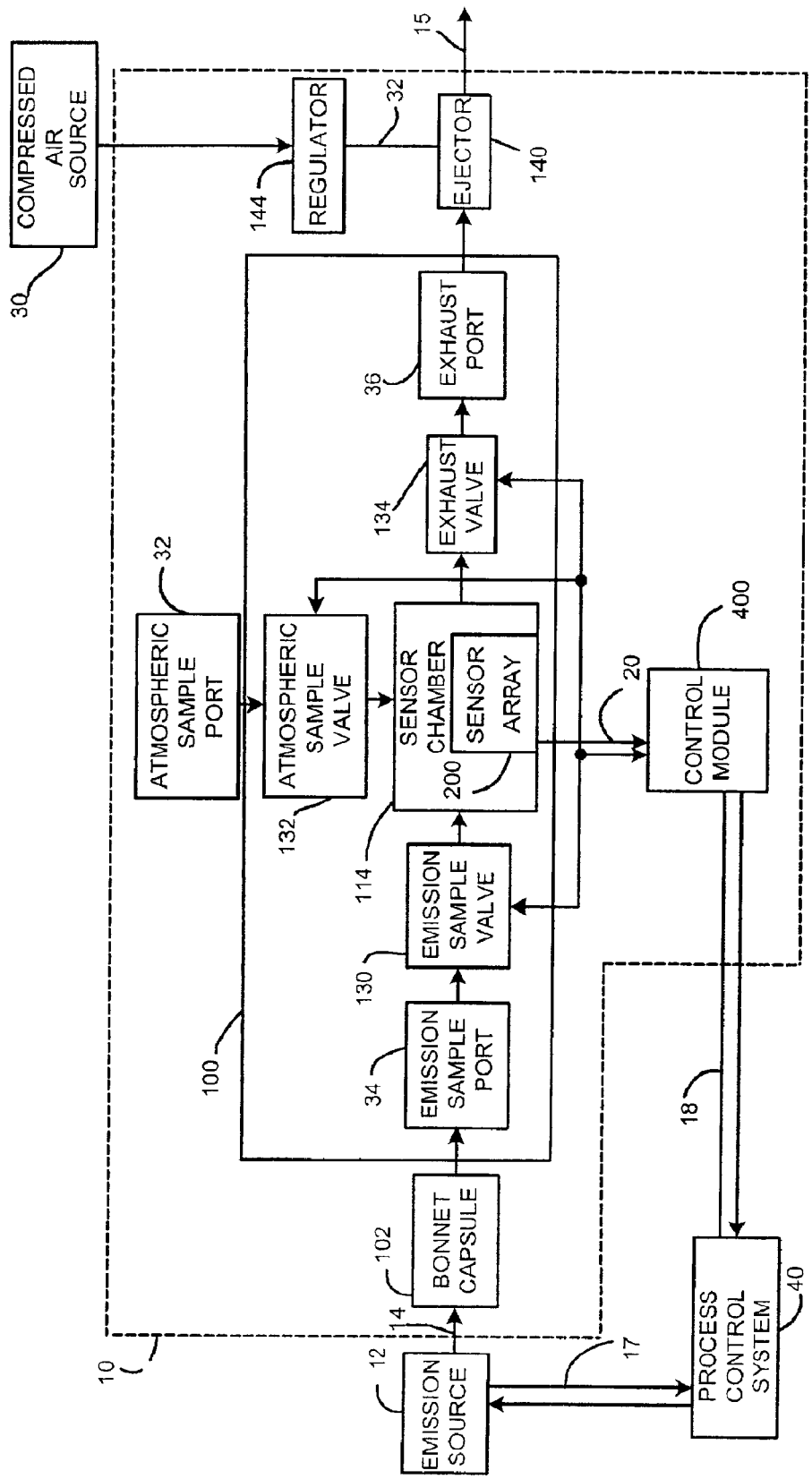
FIG. 1B is a detailed block diagram showing the major components of the sample retrieval system.

Proceeding to FIG. 1B, a more detailed illustration of the chemical detection system is shown. To accurately quantify the leak from the emission source 12, a non-contaminated source of the local plant atmosphere is collected by the system to provide a baseline or "zero concentration" exposure. To perform the collection of the zero concentration or emission sample, a pneumatic system, the sample retrieval system 100, using the compressed air source 30 has been constructed. Additional pneumatic components of the chemical detection system 10 include a bonnet capsule 102, an ejector 140, and a regulator 144. A gas sensor array 200 is located within the sensor chamber 114 of the sample retrieval system 100. The zero concentration sample is drawn into an atmospheric sample port 32 through the atmospheric sample valve 132 and into the sensor chamber 114. Typically, the gas sensor array 200 is designed to be highly sensitive to a narrow class of emissions. By creating a baseline measurement containing local atmosphere without the emission and having prior knowledge of the chemical sensor's sensitivity to the emission of interest, the chemical detection system 10 or the process control system 40 can determine the emission concentration from the emission source 12.

Continuing in FIG. 1B, the bonnet capsule 102 is comprised of an enclosure designed to envelop the surface area of the emission source 12 from which an emission is anticipated. The bonnet capsule 102 is mounted on the emission source 12 so that a gap (not shown) remains between the bonnet capsule 102 and the emission source 12. This creates a low impedance pneumatic restriction, which permits flow through the gap, through the bonnet capsule 102, and into the emission sample port 34. This flow carries any fugitive emissions emitted from the emission source into the emission sample port 34 and on into the sensor chamber 114.

During emission sample collection, the emission sample stream 14 is drawn from the bonnet capsule 102 into the sensor chamber 114, exposing the gas sensor array 200. The ejector 140 is the pneumatic device used to evacuate the sensor chamber and is known to those skilled in the art. The compressed air source 30 provides the compressed air 32 to the regulator 144. The regulator 144 provides a controlled pressure to the ejector 140. Flow through the ejector 114 creates a pressure drop thereby evacuating the sensor chamber 114 and drawing the emission sample stream 14 in at a controlled rate through the sensor chamber 114, the exhaust valve 134, the exhaust port 36 and into the ejector 140. To allow the gas sensor array 200 to respond to the emission sample, the sample is permitted to dwell within the sensor chamber 114 by closing the valves 130, 132, and 134. Clearly the appropriate actuation of the valves 130, 132, and 134 provides the chemical detection system 10 the ability to isolate and control the emission and baseline concentrations and to complete the diagnostic routines described in more detail below. Ultimately, the compressed air 32 and the emission sample stream 14 are mixed within the ejector 140 and the sample contents 15 are exhausted to the atmosphere.

Figure 1C:
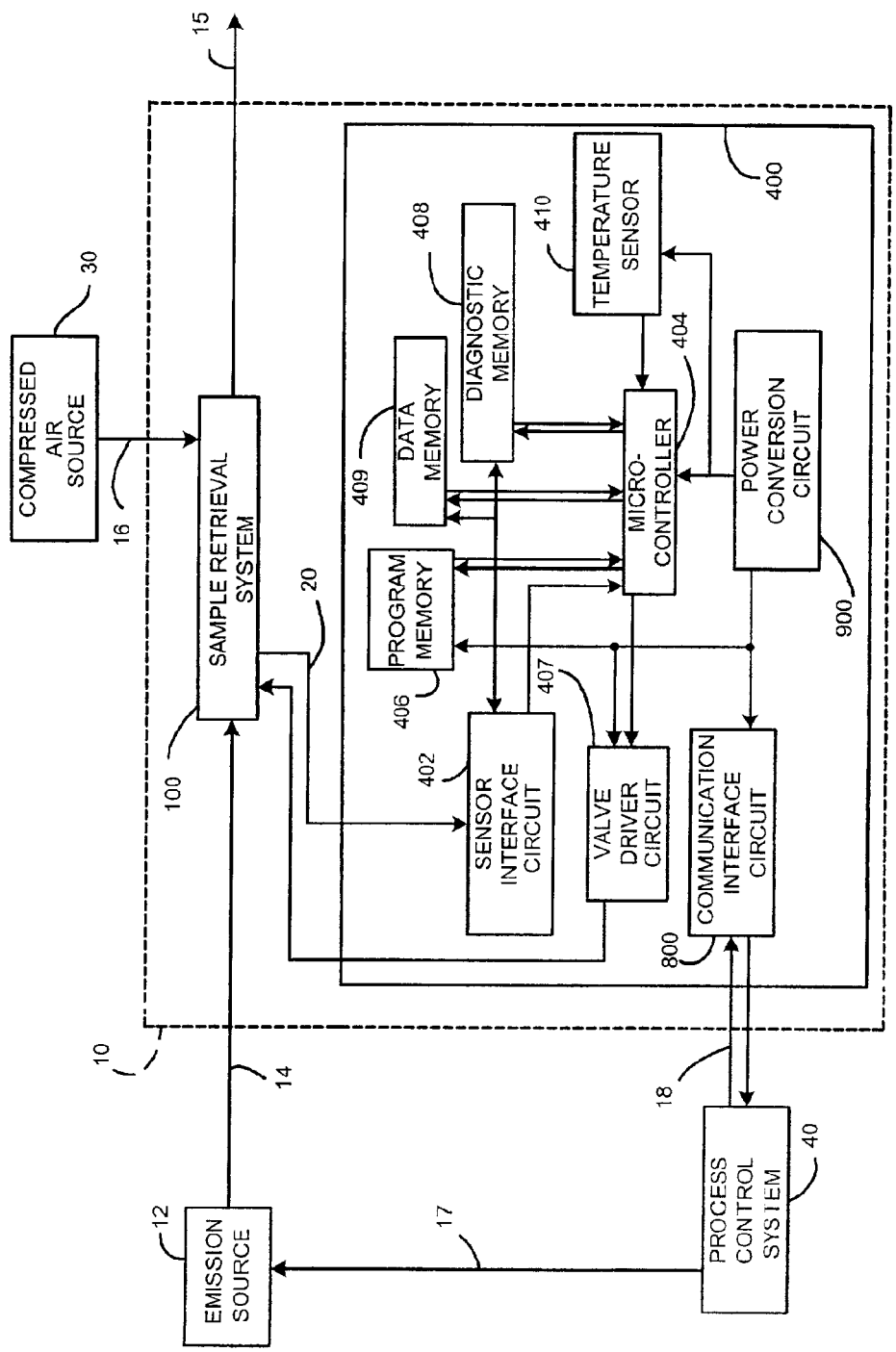
FIG. 1C is a detailed block diagram showing the major components of the communication and control circuit.

Referring now to FIG. 1C, the control and manipulation of the pneumatic hardware will now be described. The pneumatic hardware and chemical sensors contained within the present invention are operated by conventional electronic means. A control module 400 is provided to process the sensors outputs and perform control and communication for the chemical detection system 10. The control module 400 also performs the diagnostic routines, which is the subject matter of the present invention. The control module 400 includes the following components: a sensor interface circuit 402, a microcontroller 404, a program memory 406, a valve driver circuit 407, a diagnostic memory device 408, a data memory 409, a temperature sensor 410, a communication interface circuit 800, and a power conversion circuit 900.

The gas sensor array 200 is connected to the sensor interface circuit 402, which processes the signals from the gas sensor array 200 (FIG. 1B) and provides sensor data to the microcontroller 404 for diagnostic routines. The diagnostic routines are contained within the program memory 406. The temperature sensor 410, which may also be located in the sample retrieval system 100, provides temperature data used during system tests to accommodate diagnostic routine operational decisions. A suitable gas sensor and sensor interface circuit is further described in U.S. Pat. No. 6,222,366 and is assigned to Fisher Controls International, Inc. and hereby incorporated by reference According to the teaching of '366, the concentration of a fluid is measured by placing a chemical sensor formed on a Quartz Crystal Microbalance (QCM) in a fluid stream. The QCM chemical sensor is comprised of a coating or overlayer deposited on the surface of a quartz substrate with at least two electrodes deposited upon opposite sides of a flat substrate. The QCM provides a resonant network within an oscillator requiring the circuit to oscillate at the resonant frequency of the QCM. The resonant frequency is determined by counting the number of electrical transitions made by the QCM in one second. The selected coating has a preferential affinity for the emission of interest. Through various sorption processes, an increase in coating mass and a change in coating viscoelastic characteristics induce deviations in the QCM resonant frequency.

In the preferred embodiment of '366, two QCMs are connected to individual oscillator circuits. The first QCM functions as a reference device providing a resonant frequency representative of the resonant frequency of the sensing device when the sensing device is not exposed to the emission. The second QCM functions as the chemical sensor and is exposed to the emission of interest by the sample retrieval system previously described. The second QCM provides a signal proportional to the quantity of emission collected from the local environment. A digital differencing circuit is connected to the output of the two oscillator circuits and provides a signal having a frequency representative of the arithmetic difference between the resonant frequency of the sensing device and the resonant frequency of the reference device. The teachings further instruct those skilled in the art how to derive a quantitative emission measurement from the difference in device frequencies.

Returning to the present invention, the microcontroller 404 stores the chemical sensor and temperature data in the data memory 409. This data is recalled from the data memory 409 during execution of the diagnostic routines. Any fault conditions will generate an alarm. It can certainly be appreciated by those skilled in the art that communication interface circuit 800 taught in '923 can transmit the chemical sensor and temperature data directly to the process control system 40 or to a maintenance control facility not presently illustrated. Alternatively, control module 400 may operate on the data with the diagnostic routines to generate fault conditions. These fault conditions will generate diagnostic alarms. They may be stored in the diagnostic memory 408 and later recalled to report and comply with the EPA regulations, or to initiate control actions to reduce or eliminate the emissions.

The depth of the diagnostic memory 408 allows multiple diagnostic routine test results to be stored. For example, the data memory 409 of the present invention can accommodate data from 256 fault condition tests and alarms. Power conversion circuit 900 receives electrical power transmitted over the communication link by process control system 40 or provided by batteries.

Figure 2A:
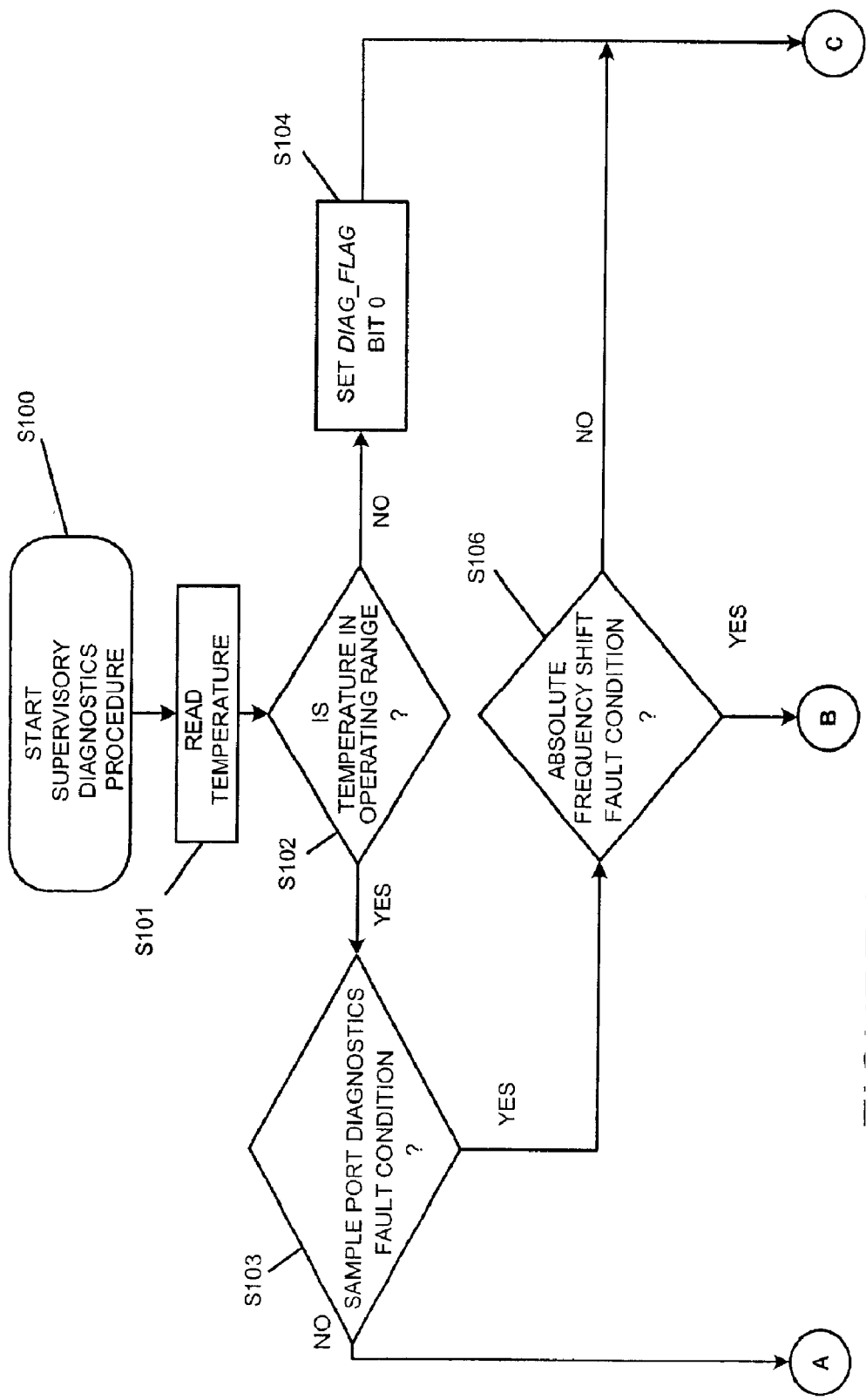
FIG. 2A and FIG. 2B are flow charts showing the logic of a supervisory diagnostic routine for a chemical detection system.
Figure 2B:
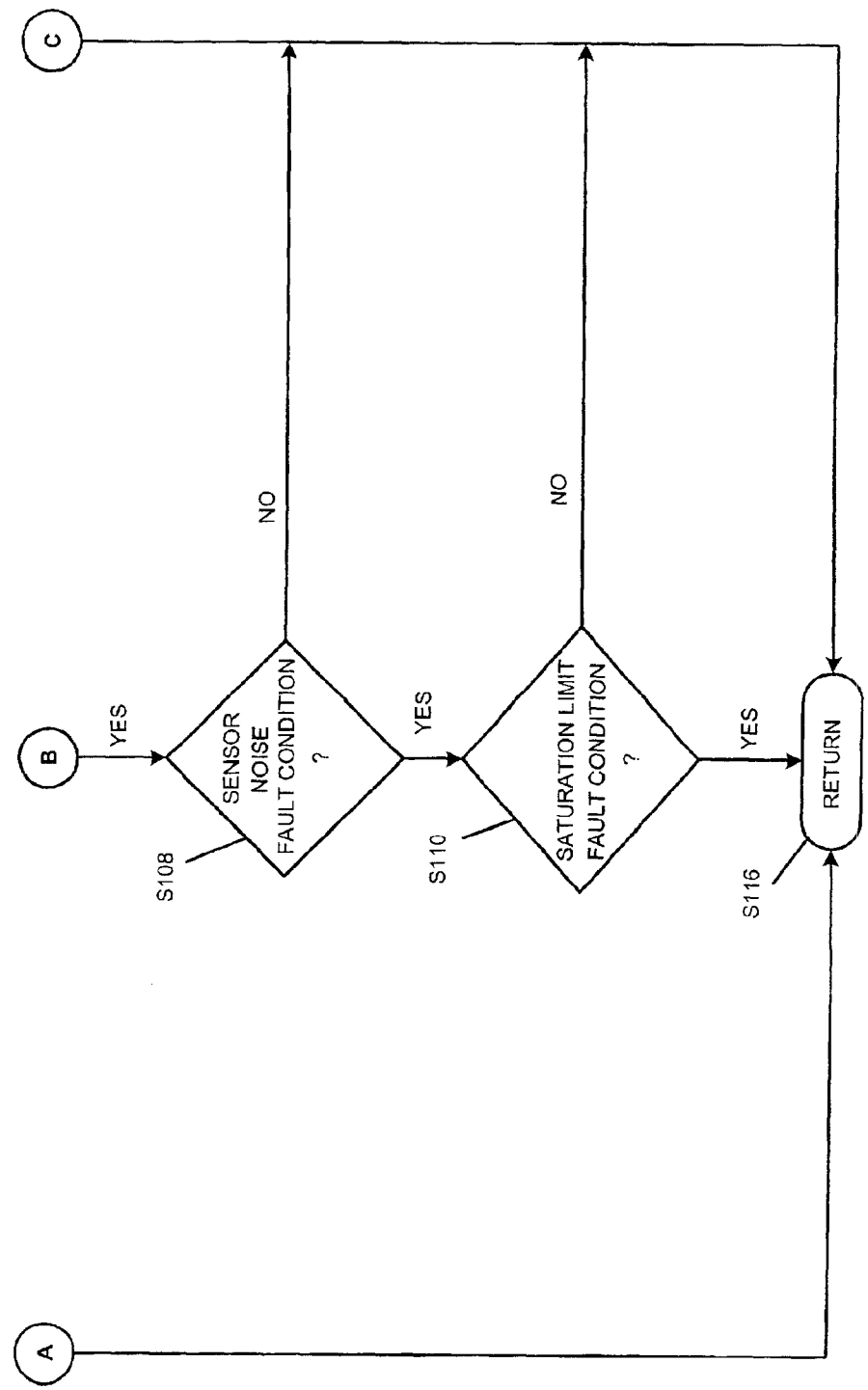

In summary, the previous passages describe the necessary system components to perform analytical measurements with field deployed instruments in industrial facilities. The present invention provides a diagnostic apparatus and diagnostic methods for a determining fault conditions within a chemical detection system. The following diagnostic methods are implemented using standard programming techniques well known to those in the art. FIGS. 2A and 2B illustrate the logic required to implement the diagnostic methods of the preferred embodiment. The routine detailed in FIGS. 2A and 2B is the supervisory diagnostic routine. This routine is invoked from a main executable program stored in the program memory 406. The main executable program always checks the diagnostic memory 408 for flagged fault conditions or alarms before proceeding with a measurement scenario. Any alarm condition will preempt the measurement scenario and will be reported by the various communication techniques previously described. There are four discrete routines executed from the supervisory diagnostic routine which utilize the apparatus and chemical sensors described above to obtain specific diagnostic information about the system and its surrounding atmospheric conditions. These routines include a sample port diagnostic routine, step S103, an absolute frequency shift fault condition routine, step S106, a sensor noise fault condition routine, step S108, and a saturation limit fault condition routine, step S110.

Figure 3A:
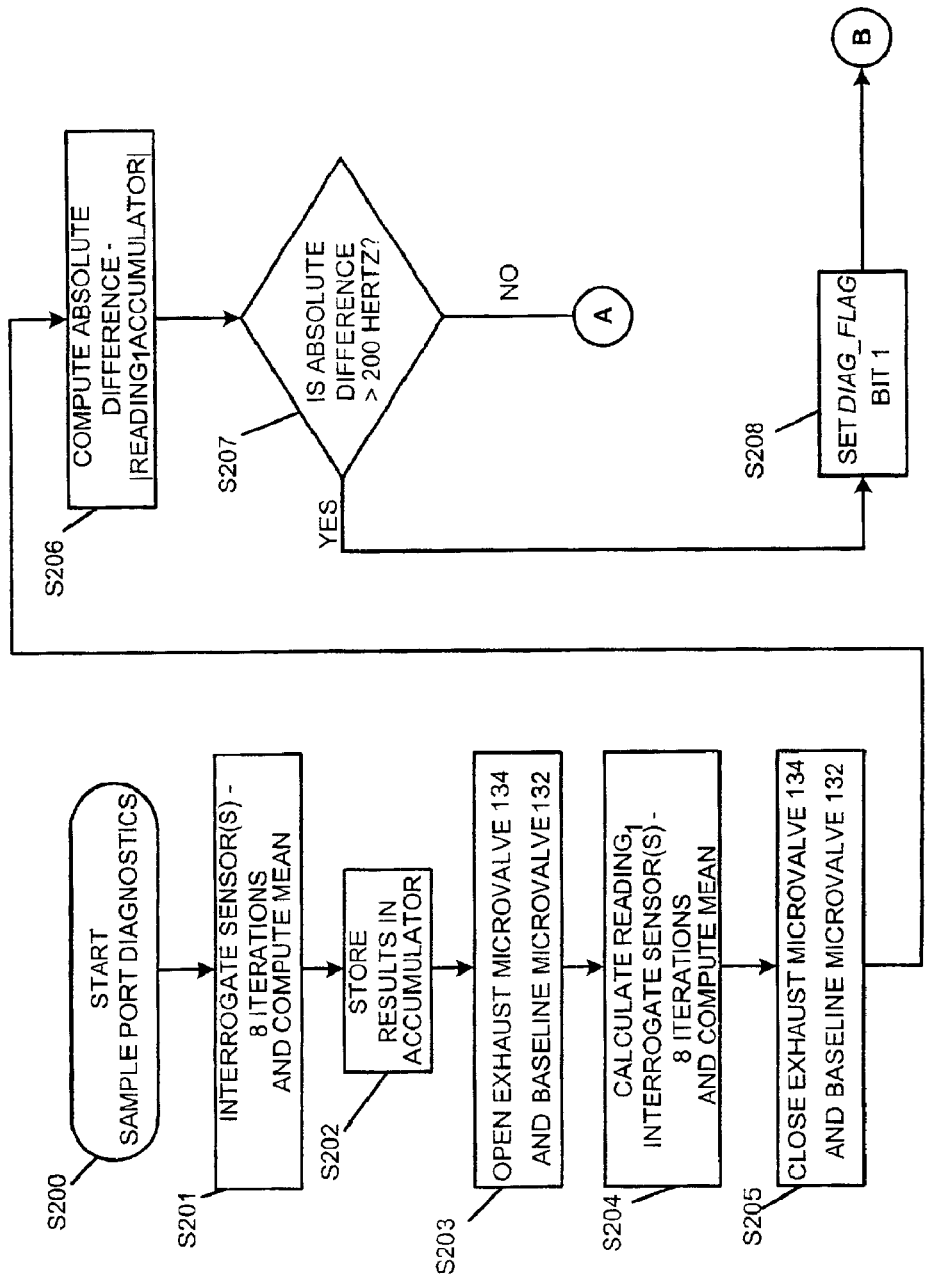
FIGS. 3A and 3B are flow charts showing the diagnostic routine for evaluating sample port obstructions in accordance with an embodiment of the present invention.
Figure 3B:
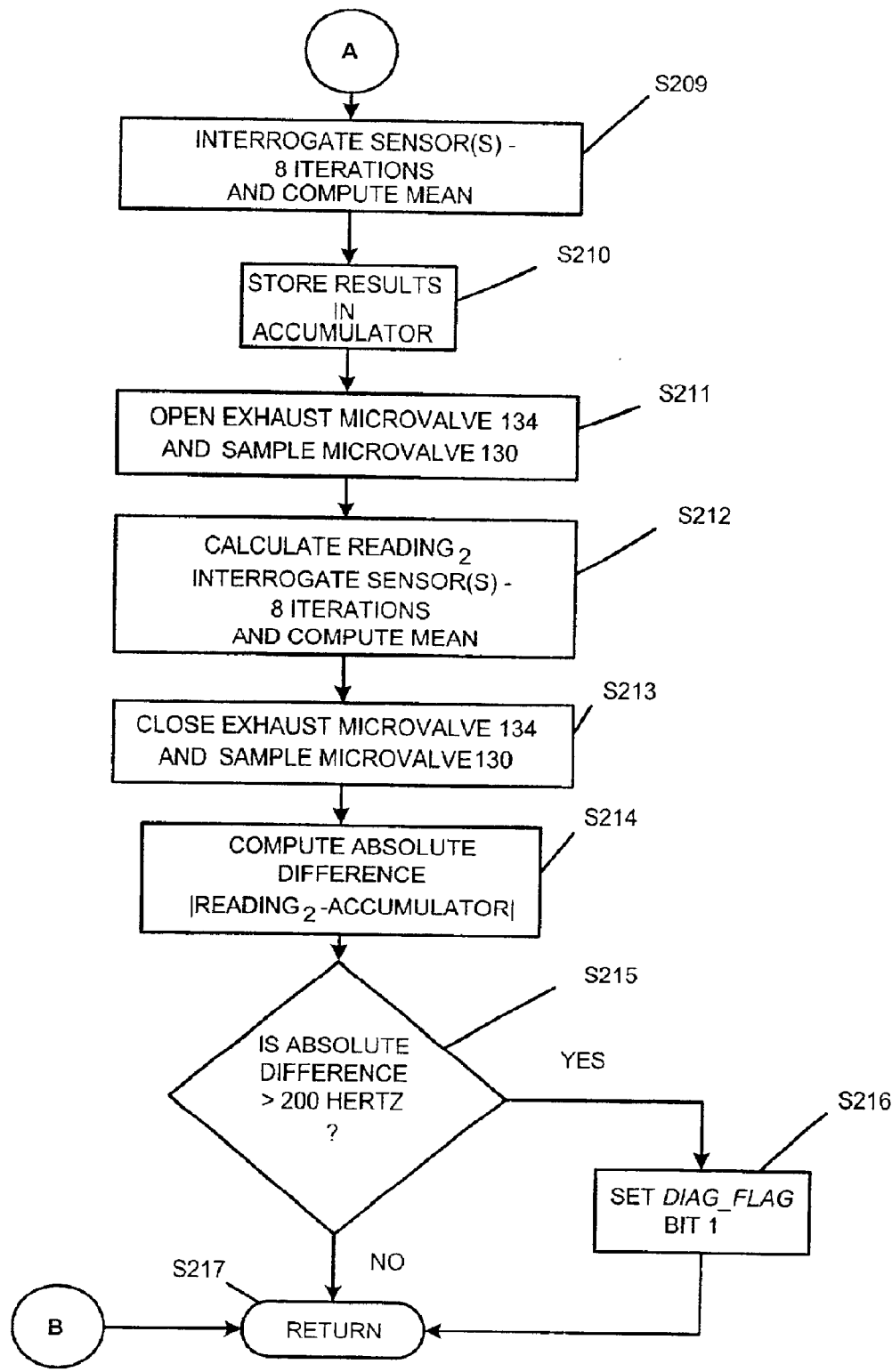

Obstructions within the system's ports or valve failures can inhibit sample retrieval system 100 flow and prevent sample collection. Failing to properly diagnose these fault conditions will be result in a complete malfunction of the chemical detection system 10. These system diagnostics rely upon the secondary sensing phenomena induced by flow upon the gas sensor array 200. By using transient response analysis on data acquired from the gas sensor array 200 during controlled exposures a very powerful diagnostic tool has been developed. The sample port diagnostic routine logic is shown in FIGS. 3A and 3B and is described in more detail below.

As previously reported, the industrial sensing environment is incredibly harsh. Undesired chemical exposures can yield permanent shifts in sensor baseline frequency. Coating delamination and particulate accumulation can produce similar effects. The diagnostic routine illustrated in FIGS. 4A and 4B demonstrates the logic required to assess these fault conditions and is described in greater detail below, step S106.

Variations in flow due to failures within the system's sample retrieval components or highly variable meteorological conditions (e.g. strong winds) during a sample acquisition can induces large deviations or noise in the gas sensor array 200 data. The diagnostic routine illustrated in FIGS. 5A and 5B demonstrates the logic required to assess these fault conditions and is described in greater detail below, step S108.

Figure 6A:
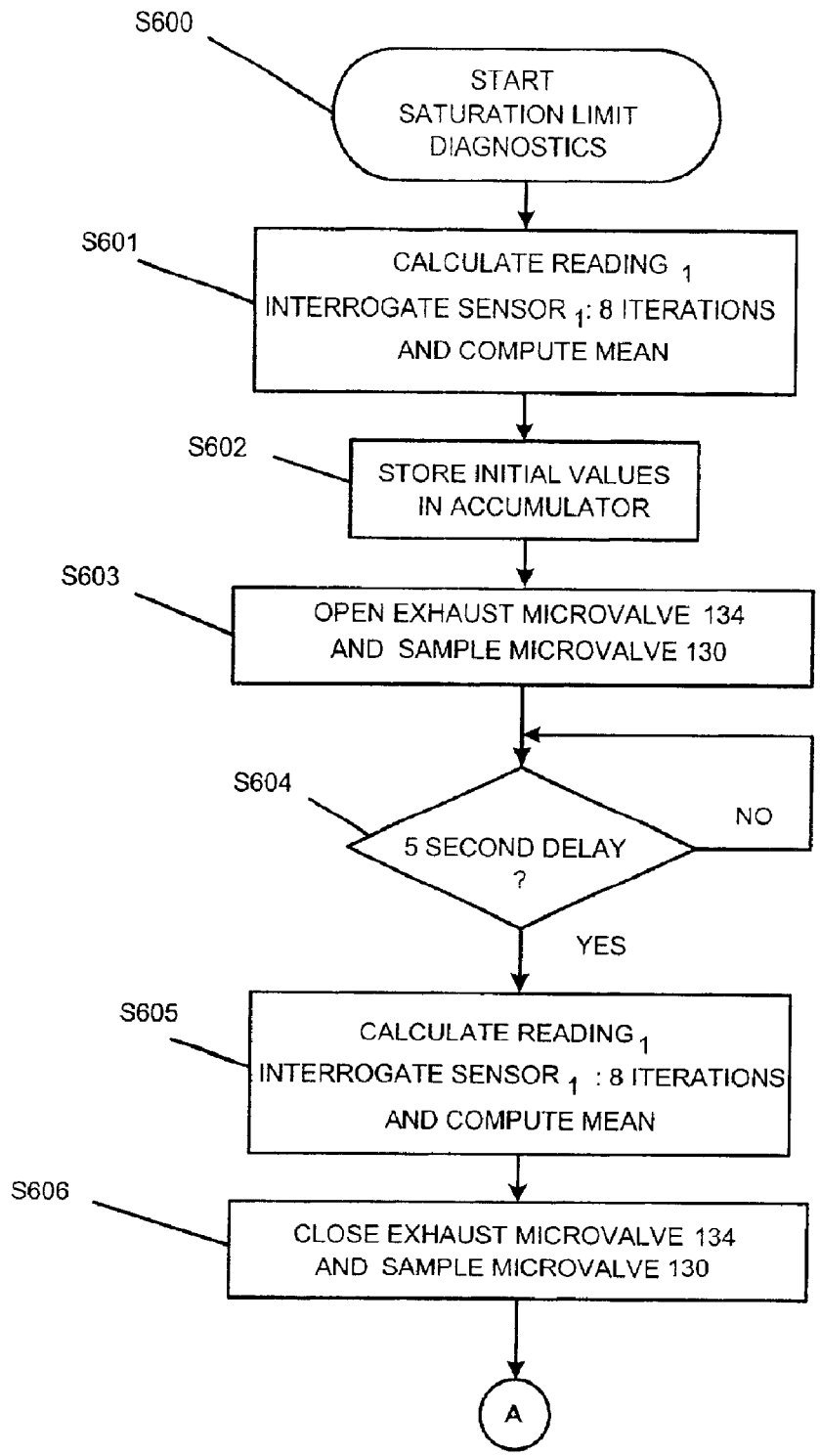
FIGS. 6A and 6B are flow charts showing the diagnostic routine for determining the chemical sensor saturation potential.
Figure 6B:
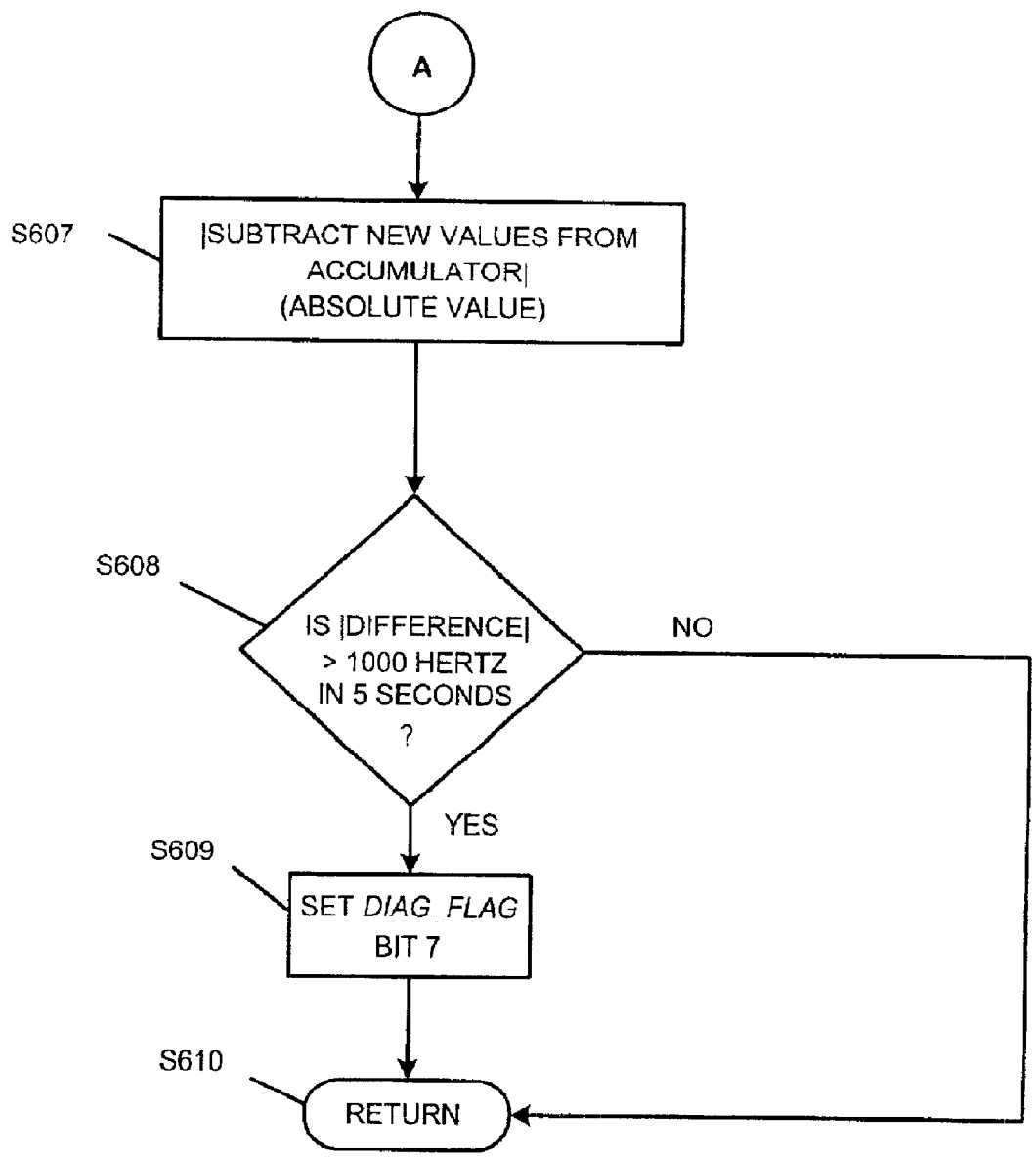

Finally, excessive emission source 12 leaks can irreparably harm the chemical sensors. As previously described, high concentrations of the emission can damage or even remove the sensitive coatings from the sensor. Those skilled in the art refer to these high concentrations as the saturation limit of the chemical sensor. The necessary logic to determine the saturation potential is shown in FIGS. 6A and 6B and is described in greater detail below, step S110.

The supervisory diagnostic routine represented by FIGS. 2A and 2B would typically be called by a main executable program operating in the control module 400 prior to every measurement scenario and the reporting of any emission data. All routines are stored in the program memory 406. The preferred embodiment demonstrates the order and specific routines to be executed for diagnostic validation of the chemical detection system 10. Clearly, diagnostic information can still be obtained if the sequence of operation is changed or if less than of the total number of diagnostic routines is performed. Upon completion, the supervisory diagnostic routine returns to the main executable program for resumption of a measurement survey if no fault conditions were detected.

Upon entry into the supervisory routine, the temperature sensor 410 determines the ambient temperature, step S101. The temperature sensor 410 presents a digital representation of the ambient temperature preferably (although not required) in degrees Celsius to the microcontroller 404. As gas sensor array 200 performance is dependent upon temperature, the diagnostic routine determines if the ambient temperature is within a proscribed operating range, for example from −10 to +50 Celsius, step S102. If the temperature is outside the operating range, a memory register in diagnostic memory 408, designated diag_flag, will have a bit set or flagged to designate an invalid operating range, step S104, and the routine is exited, step S116. Any flagged or detected fault condition will establish an alarm, interrupting the diagnostic routine, and exit to the main executable program.

Figure 7:
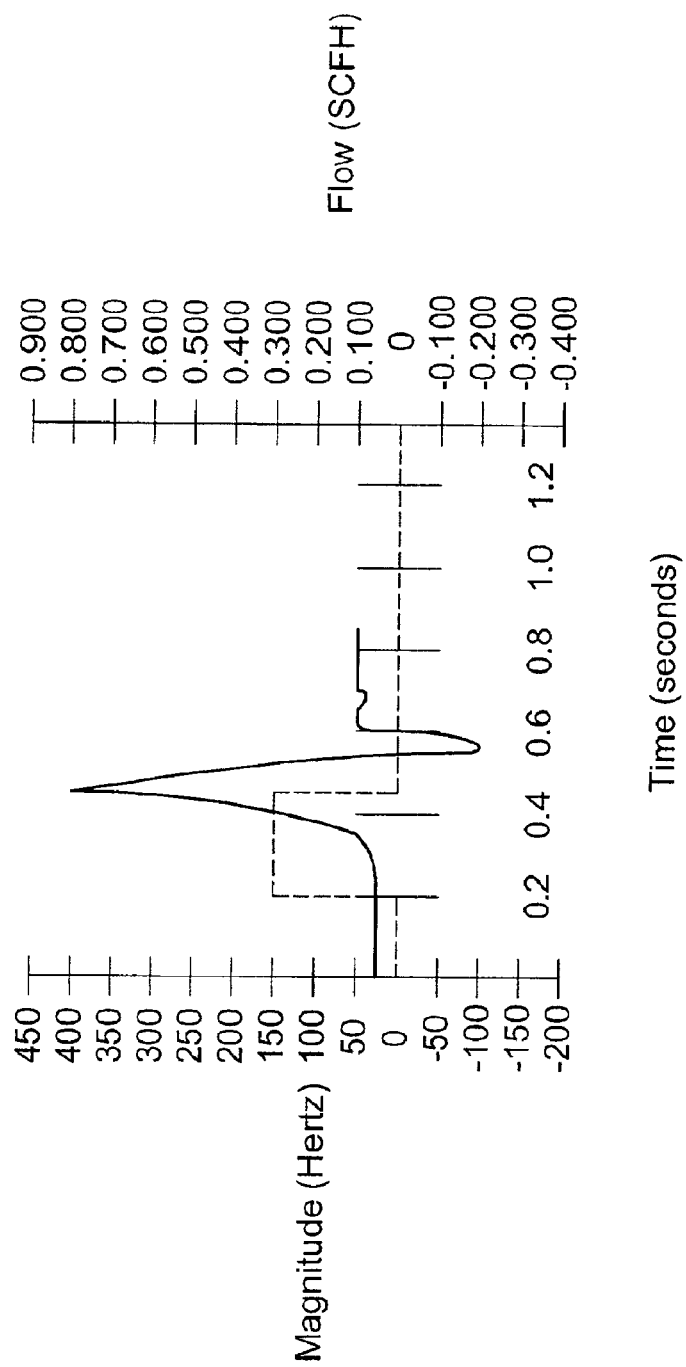
FIG. 7 is a graphical illustration of the transient response behavior of a QCM chemical sensor to an abrupt change in thermodynamic conditions.
Figure 1A:
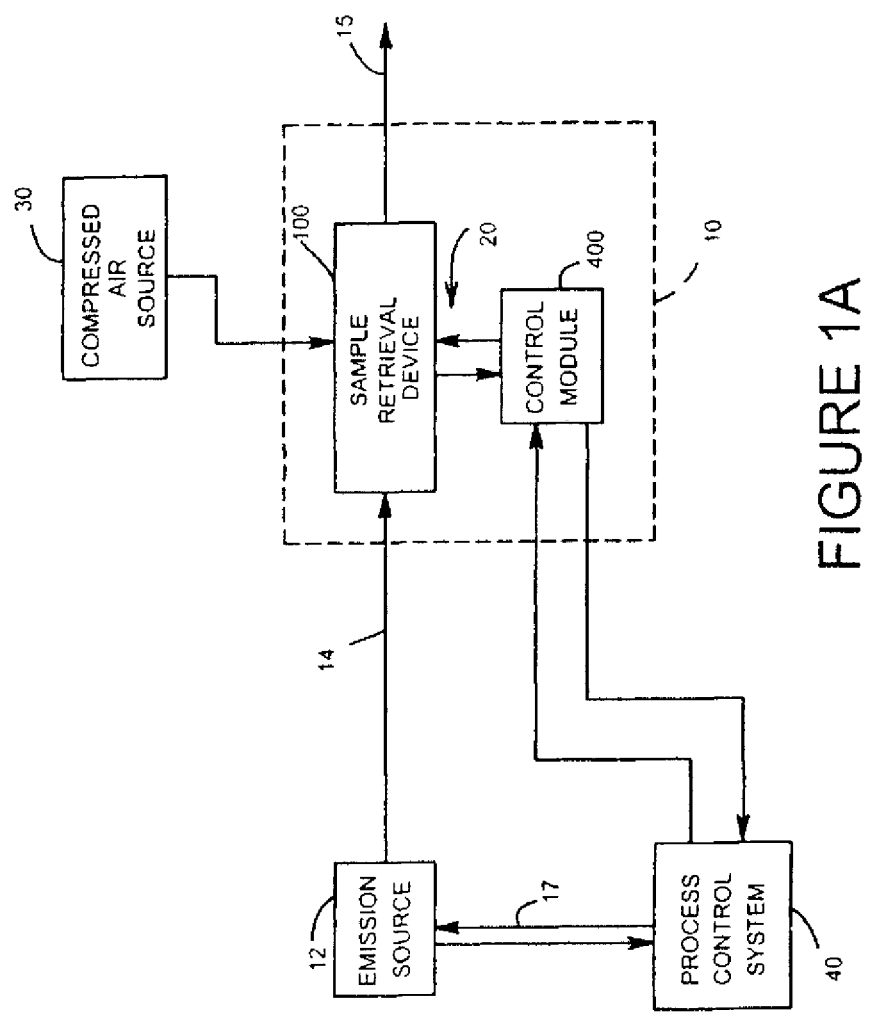
Figure 1B:
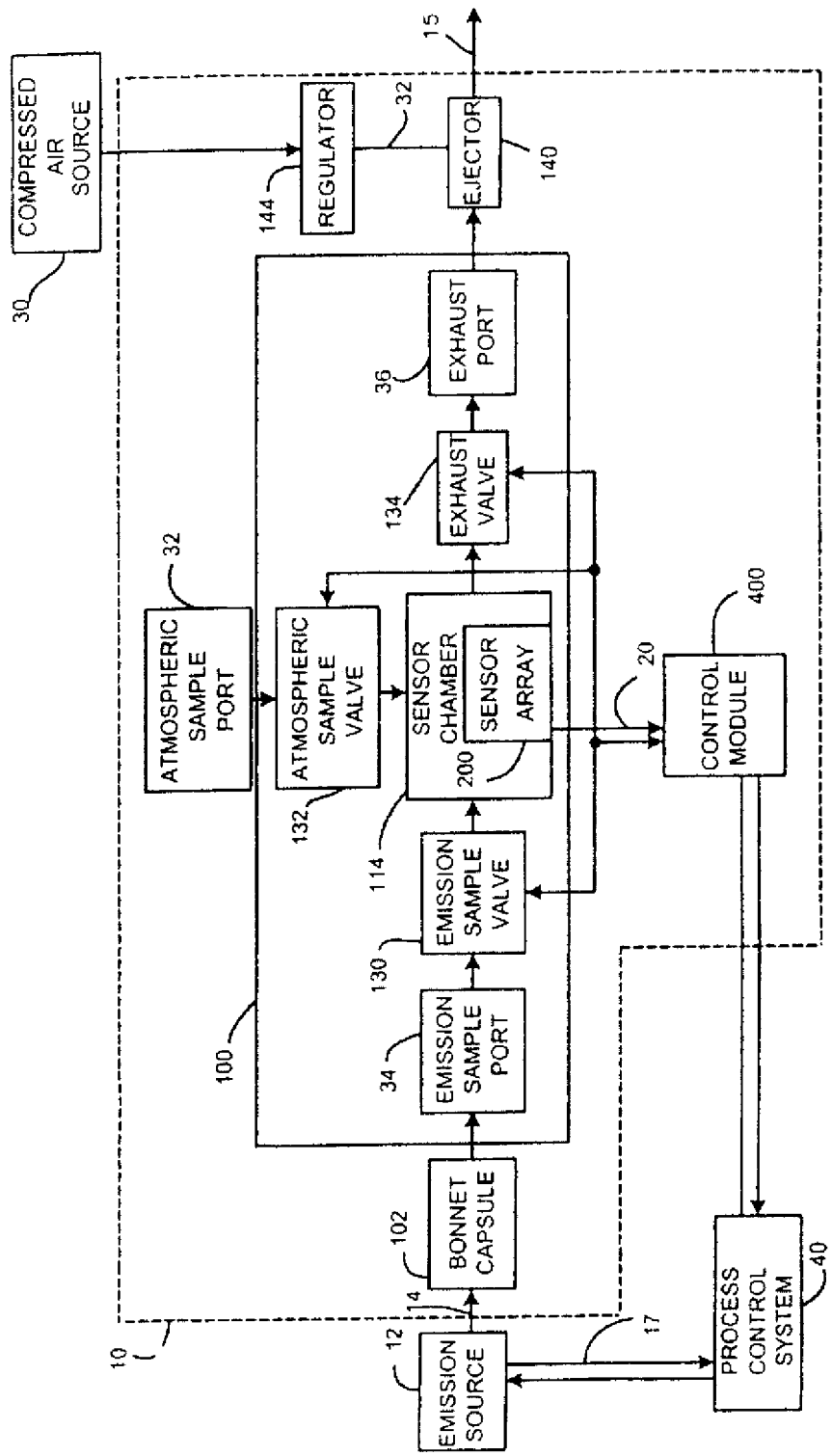
Figure 1C:
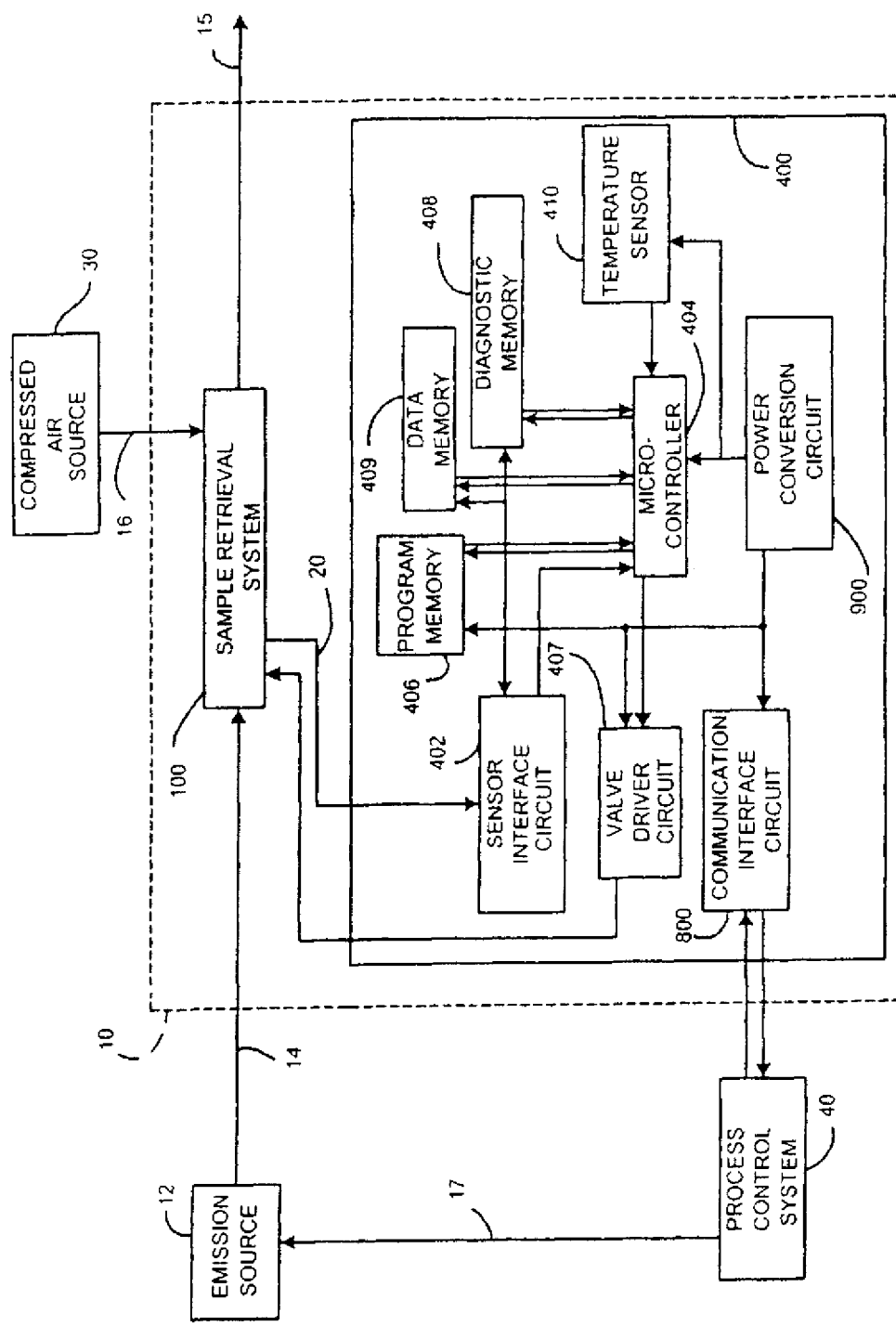
Figure 2A:
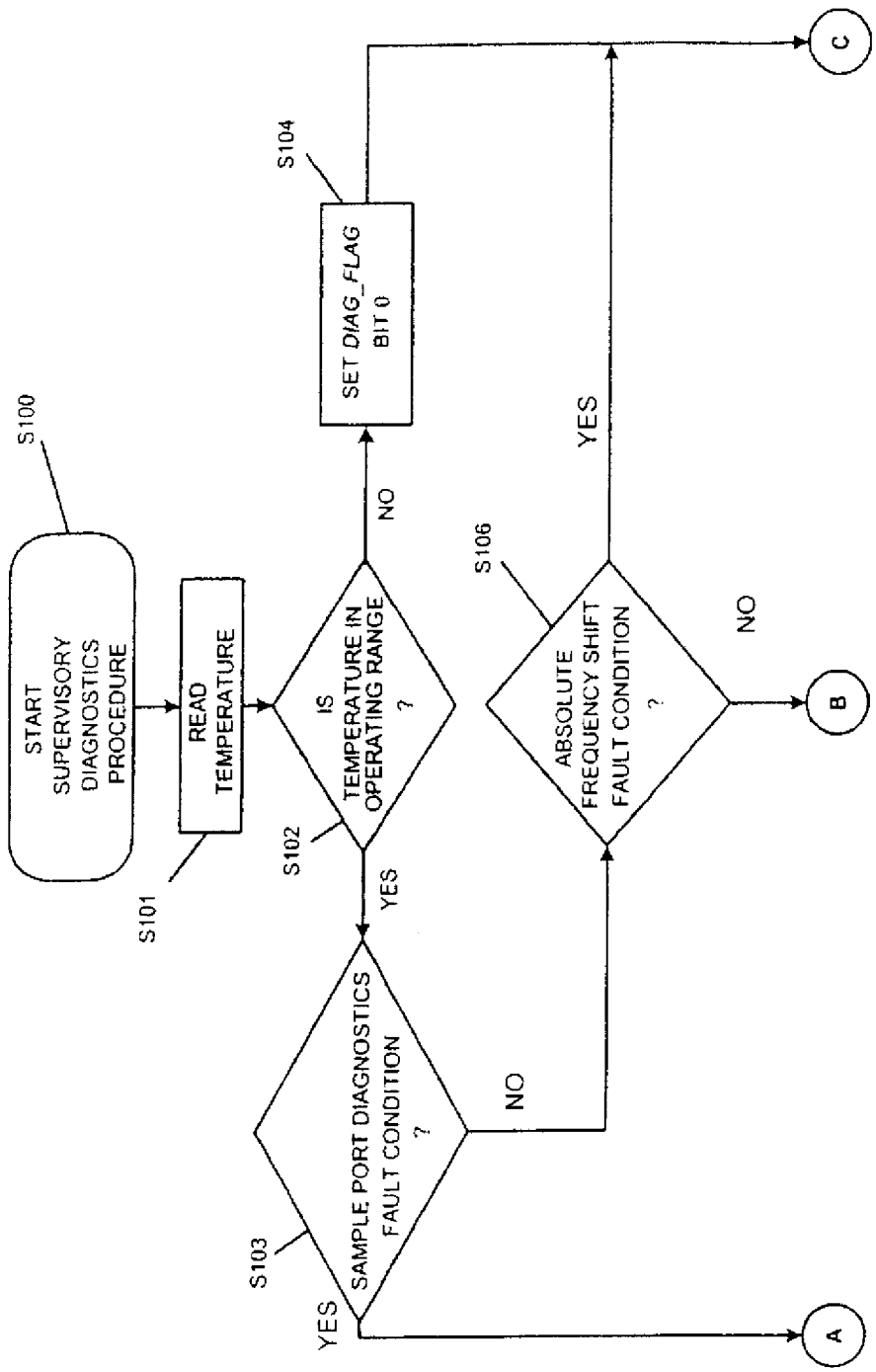
Figure 2B:
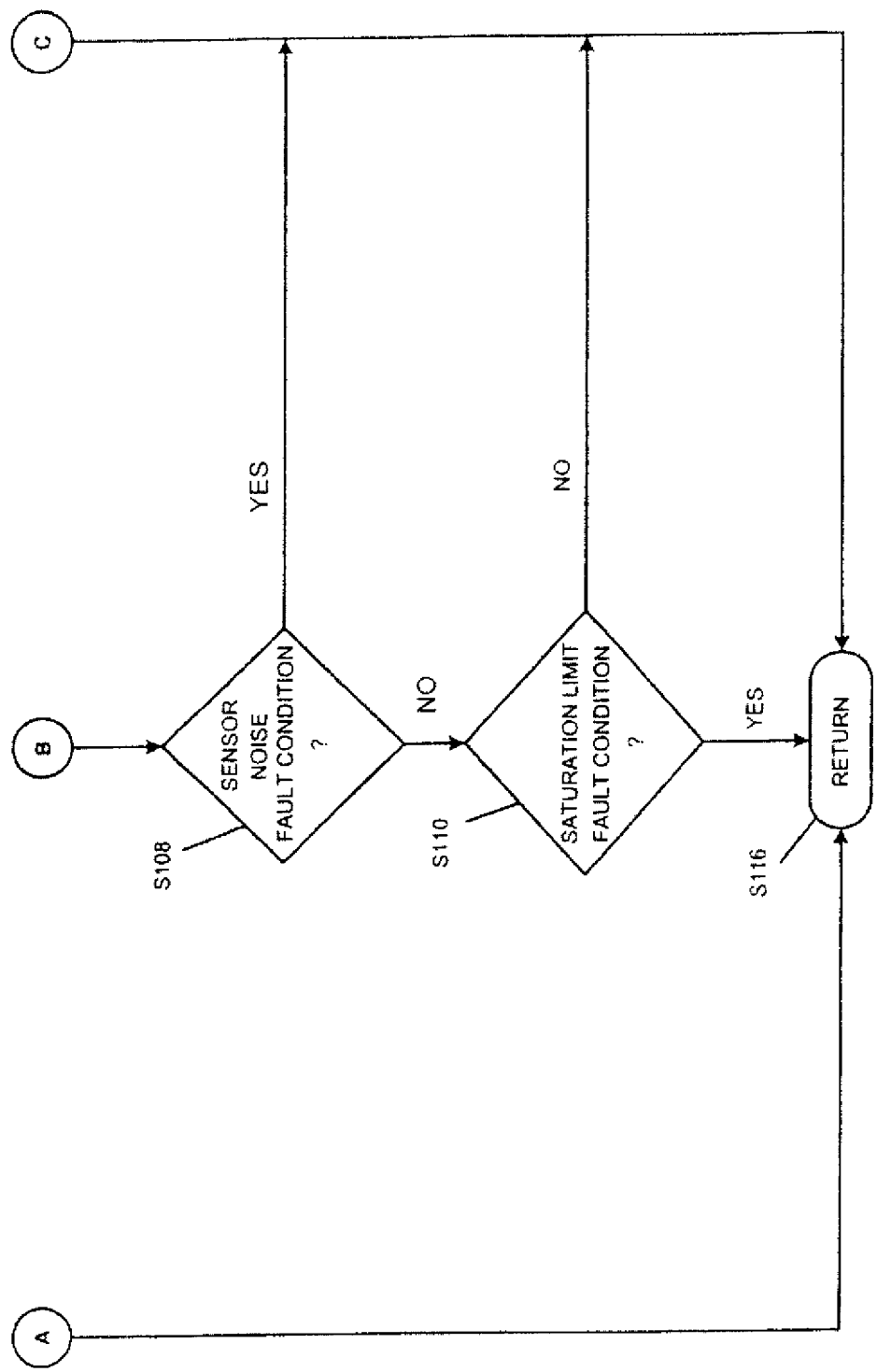
Figure 3A:
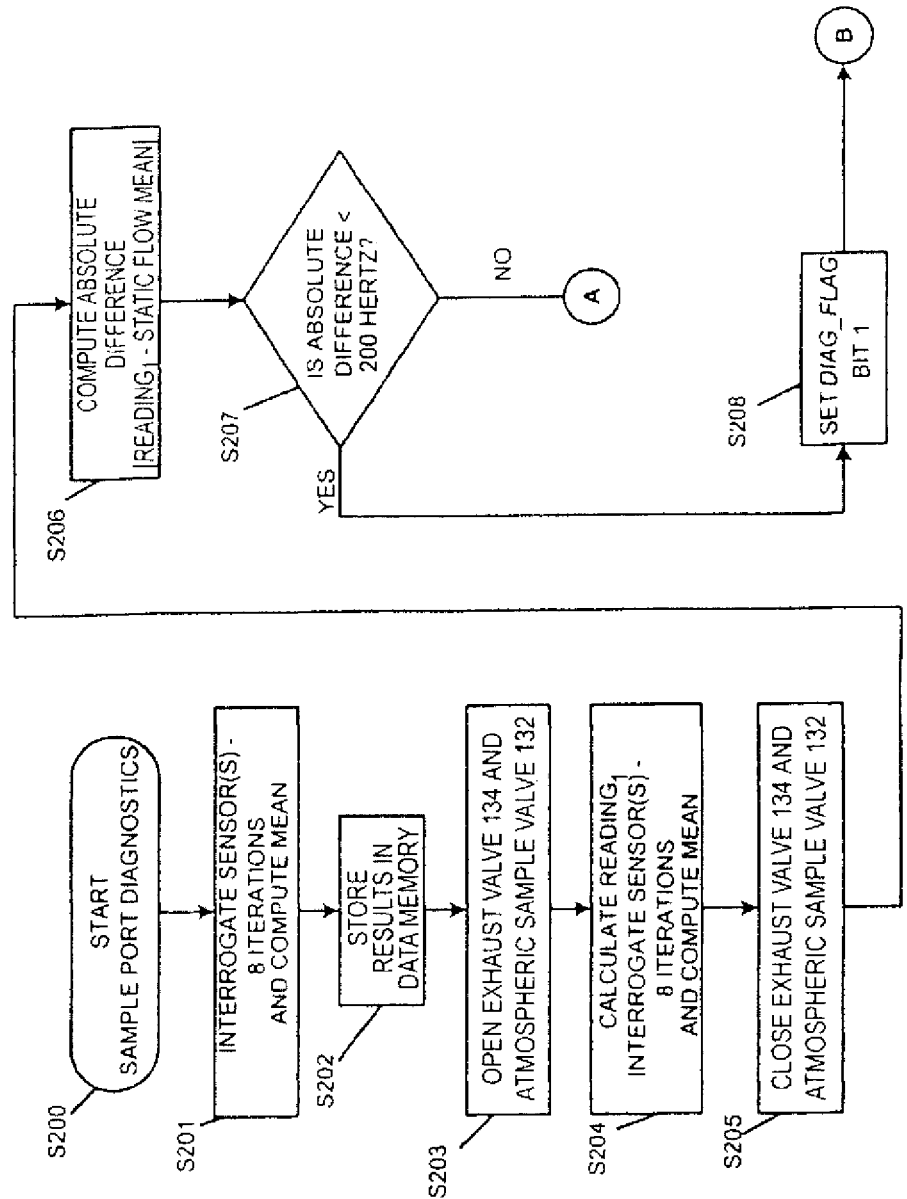
Figure 3B:
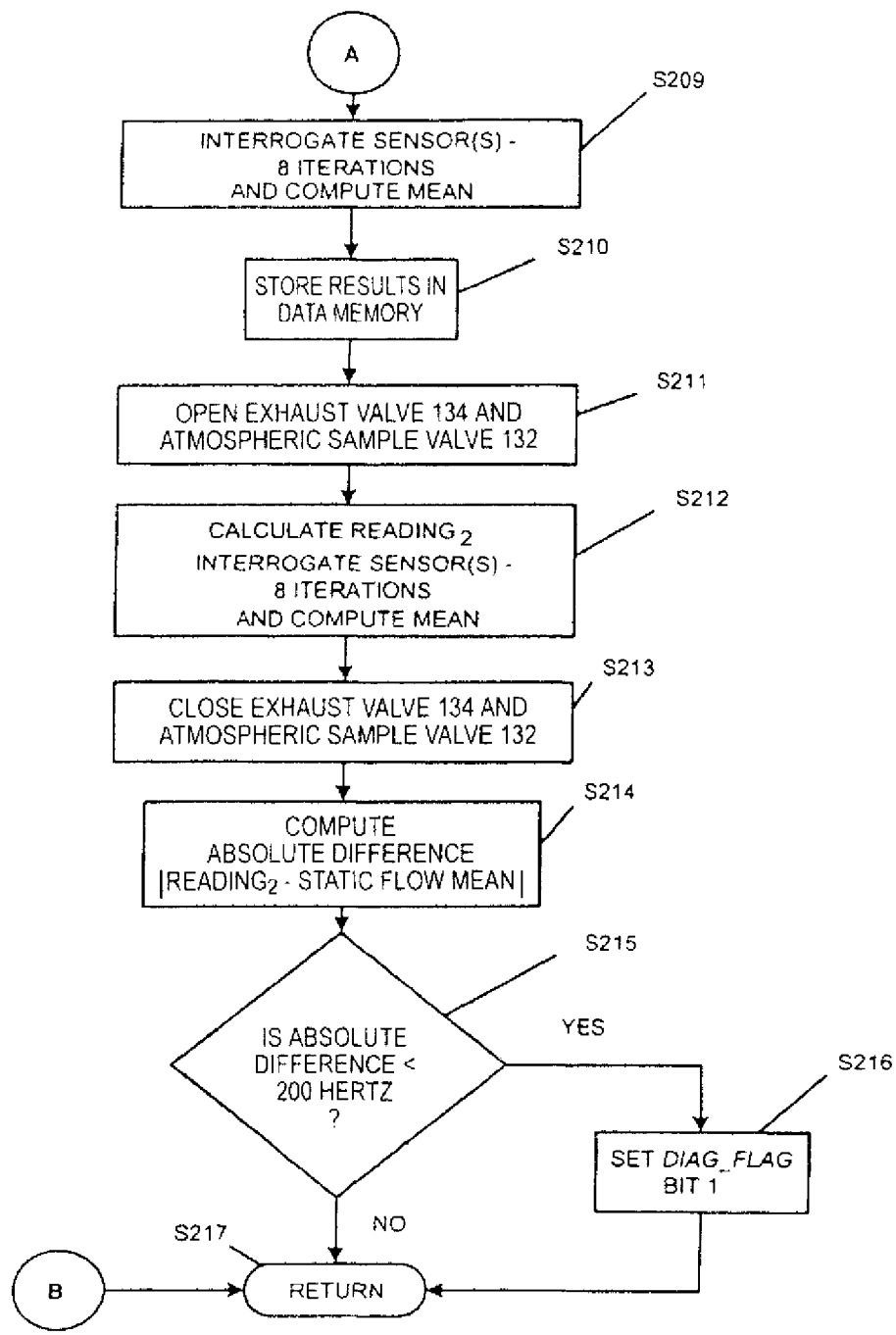
Figure 4B:
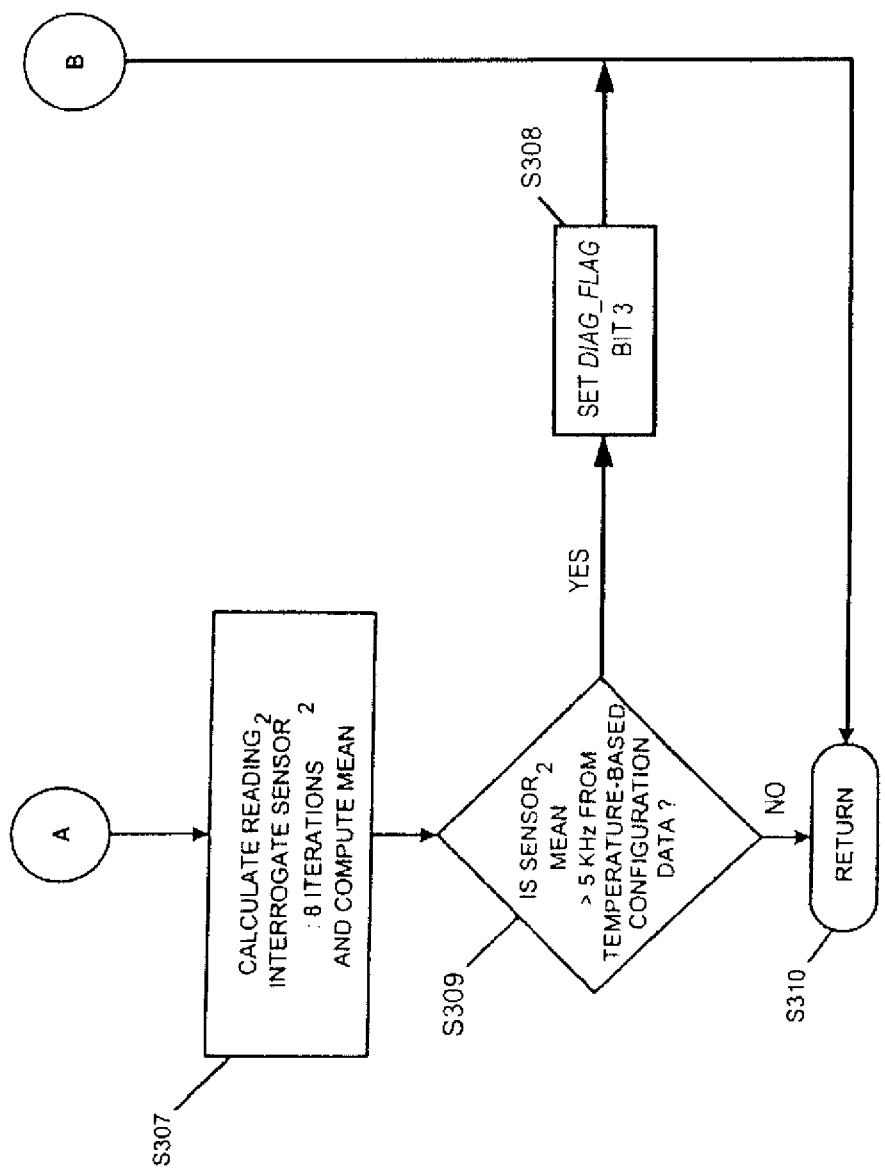
Figure 5B:
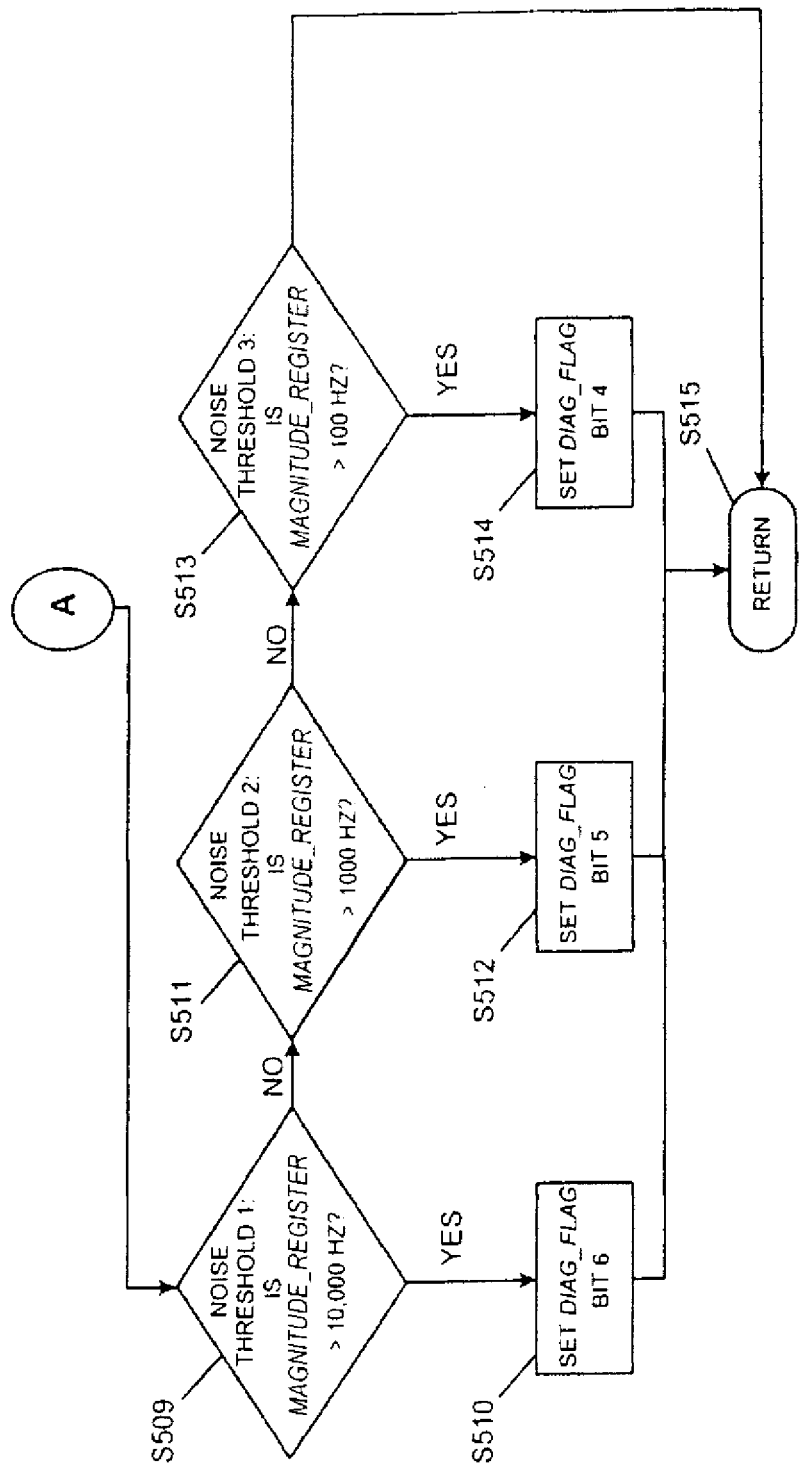
Figure 6A:
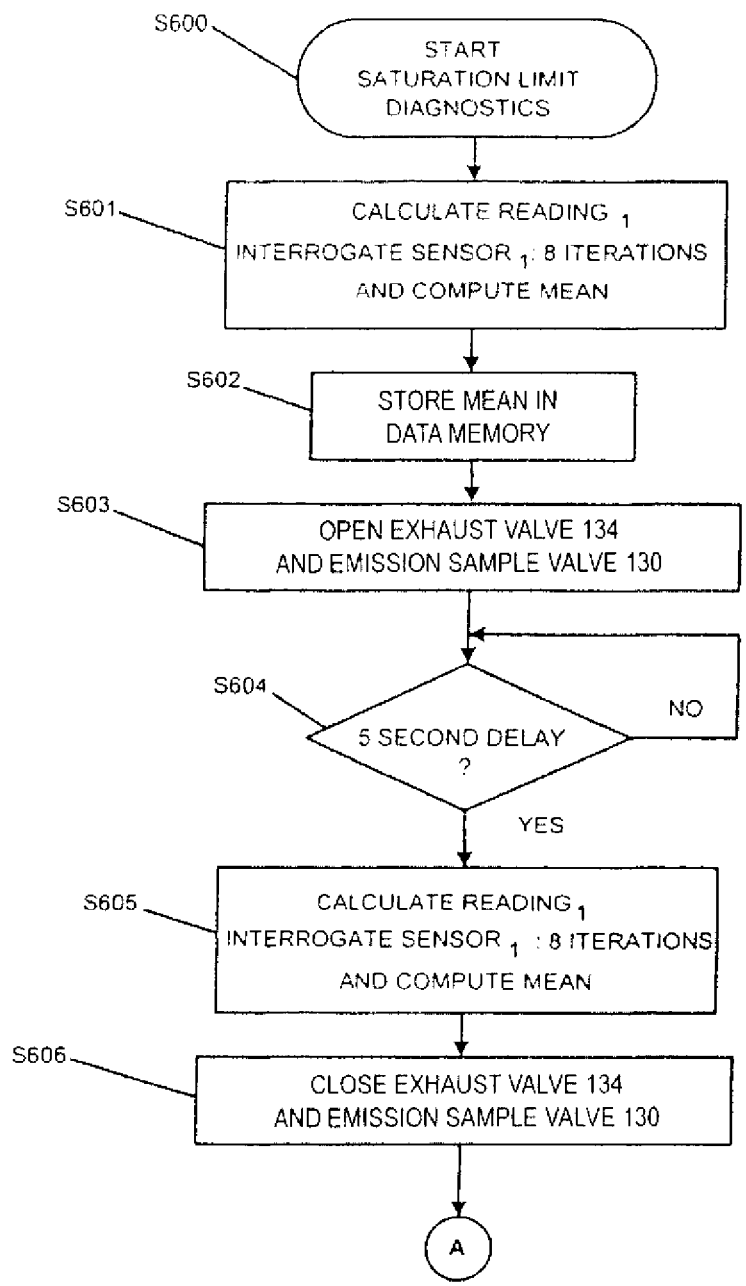
Figure 6B:
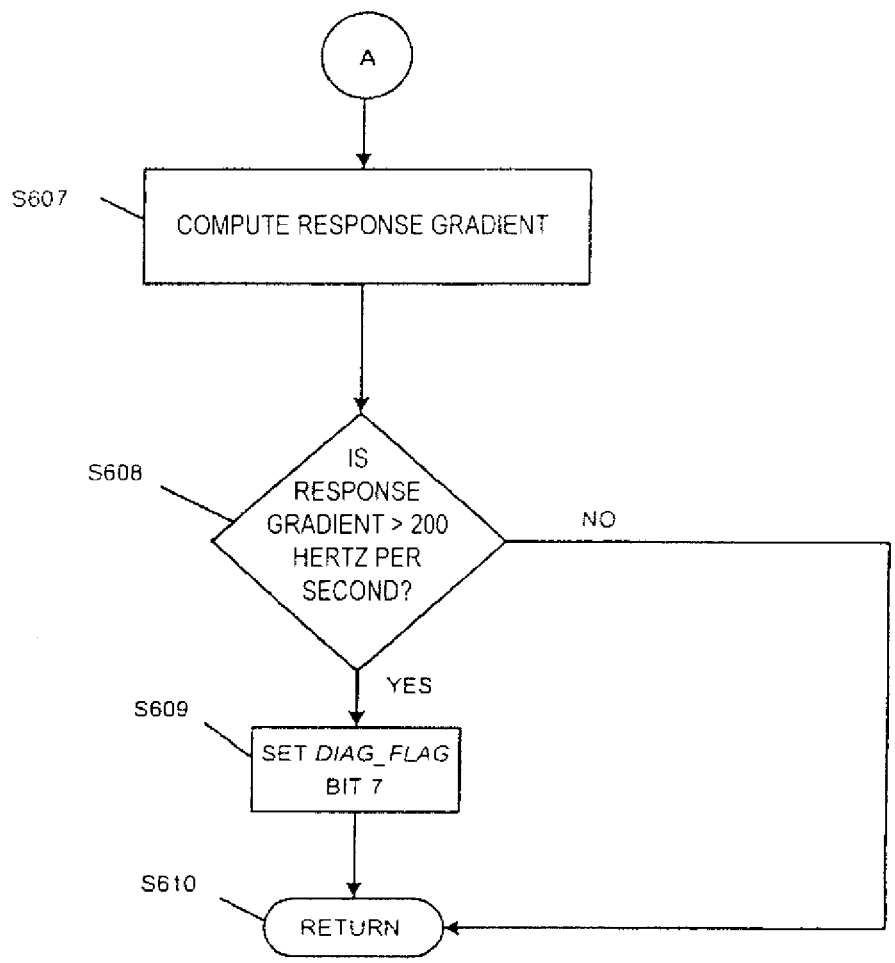

If the temperature is within the desired operating range, the sample port diagnostic routine is invoked, step S103. If a fault condition is detected in the sample port diagnostic routine the condition is flagged in diag_flag and the supervisory routine is exited, step S116. If no fault condition is detected, execution proceeds to the absolute frequency shift diagnostic routine, step S106. If an absolute frequency shift fault condition does not result, execution vectors to the noise threshold diagnostic routine, step S108. Upon successful completion of the noise threshold diagnostic routine, the saturation limit diagnostic routine is executed, step S110. The successful completion of the four diagnostic routines return program flow to the main executable program operated by control module 400, step S116. Continuing in more detail, FIGS. 3A and 3B illustrate the sample port diagnostic routine. This routine is based upon transient flow phenomena exhibited by the gas sensor array 200. For example, the chemical sensors as described in '366 patent have a transient flow sensitivity of approximately 69 ppm per scfh. As depicted in FIG. 7, abrupt changes in flow will produce a transient response, the transient flow phenomena, in sensor data (e.g. a step change from static flow to 200 sccm flow will produce a transient sensor response of about 450 Hertz on a 15 MHz substrate). Therefore, by manipulating the sample retrieval system components to induce a step change in flow while simultaneously acquiring and analyzing the gas sensor array 200 response data, a flow fault condition can be detected. The underlying logic is as follows: if any of valves 130, 132, or 134, has either a partial or total obstruction such that flow is degraded, the measured transient behavior of the gas sensor array 200 will be less than the "threshold" condition of specified in the diagnostic routine. Additionally, any valve actuation failures will yield similar flow disruptions.

Accurately determining the presence of the fault condition requires interrogating or collecting eight sensor readings, step S201. Due to the uncorrelated nature of the gas sensor array 200 noise, the eight sequential sensor readings from the sensor interface circuit 402 are used to compute an arithmetic mean or "average" to reduce the noise. Noise "spikes" in the data can cause false alarms. The sensor arithmetic mean is stored in a register within the data memory 409, step S202. Microcontroller 404 controls the valves 130, 132, and 134 through valve driver circuit 407 to enable different flow scenarios during sample collection. Valve driver circuit 407 is a typical h-bridge driver well known to those in the art.

Microcontroller 404 opens the exhaust valve 134 and the atmospheric sample valve 132, step S203. As previously explained, the ejector 140 evacuates the sensor chamber 114, thereby drawing in baseline atmosphere into the sensor chamber 114, exposing the gas sensor array 200 to an abrupt increase in flow. When sample port 32 on atmospheric sample valve 132 or the exhaust valve 134 has no obstructions and the valves operate correctly, the expected transient response of behavior of the gas sensor array 200 occurs. The transient behavior of the gas sensor array 200 typically occurs in less than two seconds and is depicted in FIG. 7. Eight sequential readings, under dynamic flow conditions, are taken and the mean is calculated and placed in an internal memory register in the microcontroller 404, step S204. Thereafter, the exhaust valve 134 and the atmospheric sample valve 132 are closed, step S205. Next, the absolute difference between the arithmetic mean from the baseline reading during static flow and the arithmetic mean during the abrupt change in flow is computed, step S206. Adequate flow within the system will produce a transient response greater than a specified value under all operational conditions. In the diagnostic routine, a conditional test determines if the range of the absolute difference is less than a predetermined value, for example 200 Hertz, step S207. A fault condition is detected if the conditional test results are positive, step S208, otherwise the test continues to evaluate the next sensor, steps S209–S216. FIGS. 3A and 3B depicts the logic for a chemical detection system 10 with two sensors, but it should be appreciated by those skilled in the art that the same logic can apply to a single sensor or a plurality of sensors. Fault conditions are handled as previously described. Upon completion, program execution is returned to the supervisory diagnostic procedure, step S217.

Figure 4A:
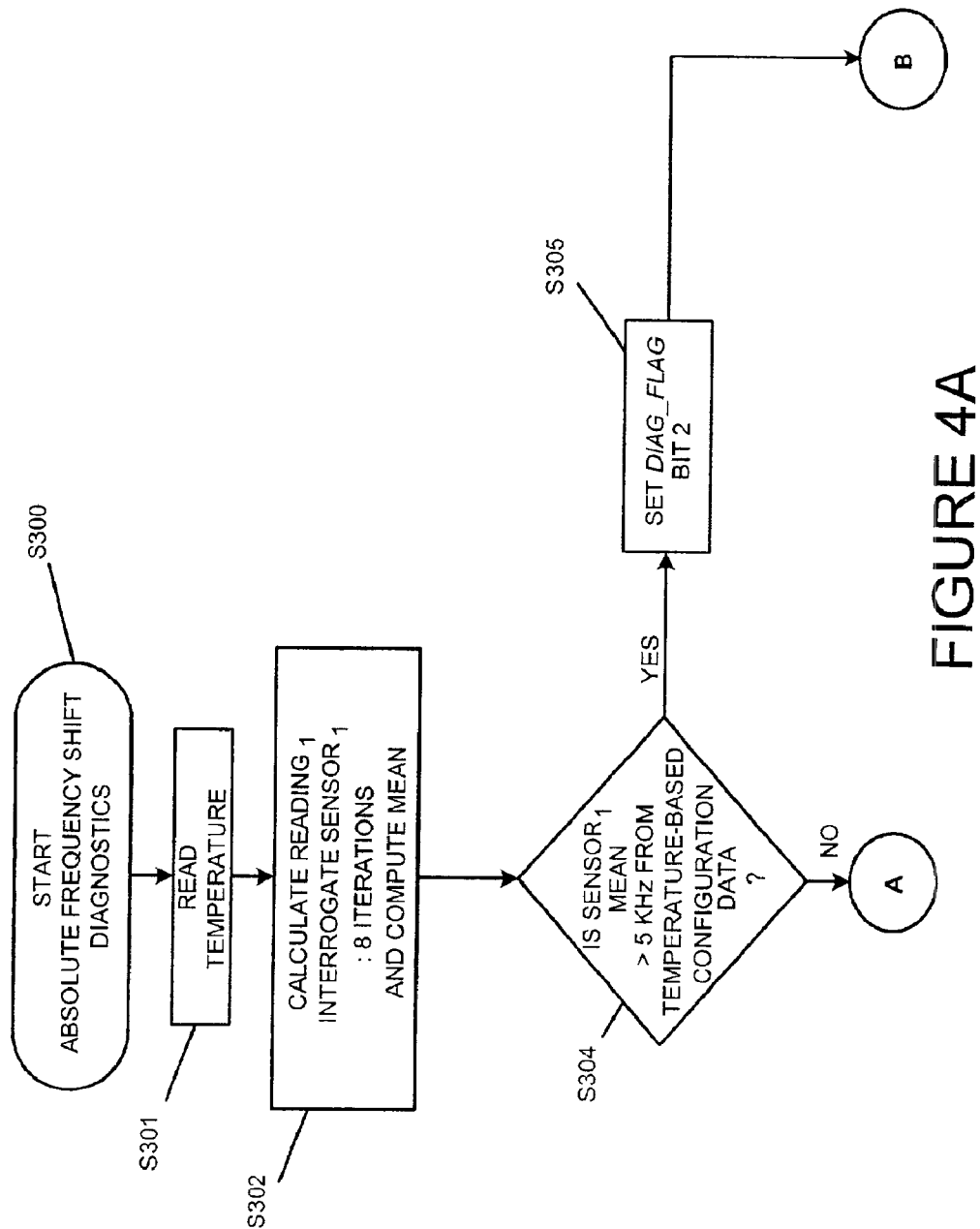
FIGS. 4A and 4B are flow charts showing the implementation of a diagnostic routine used to determine absolute frequency shifts in QCMs.
Figure 4B:
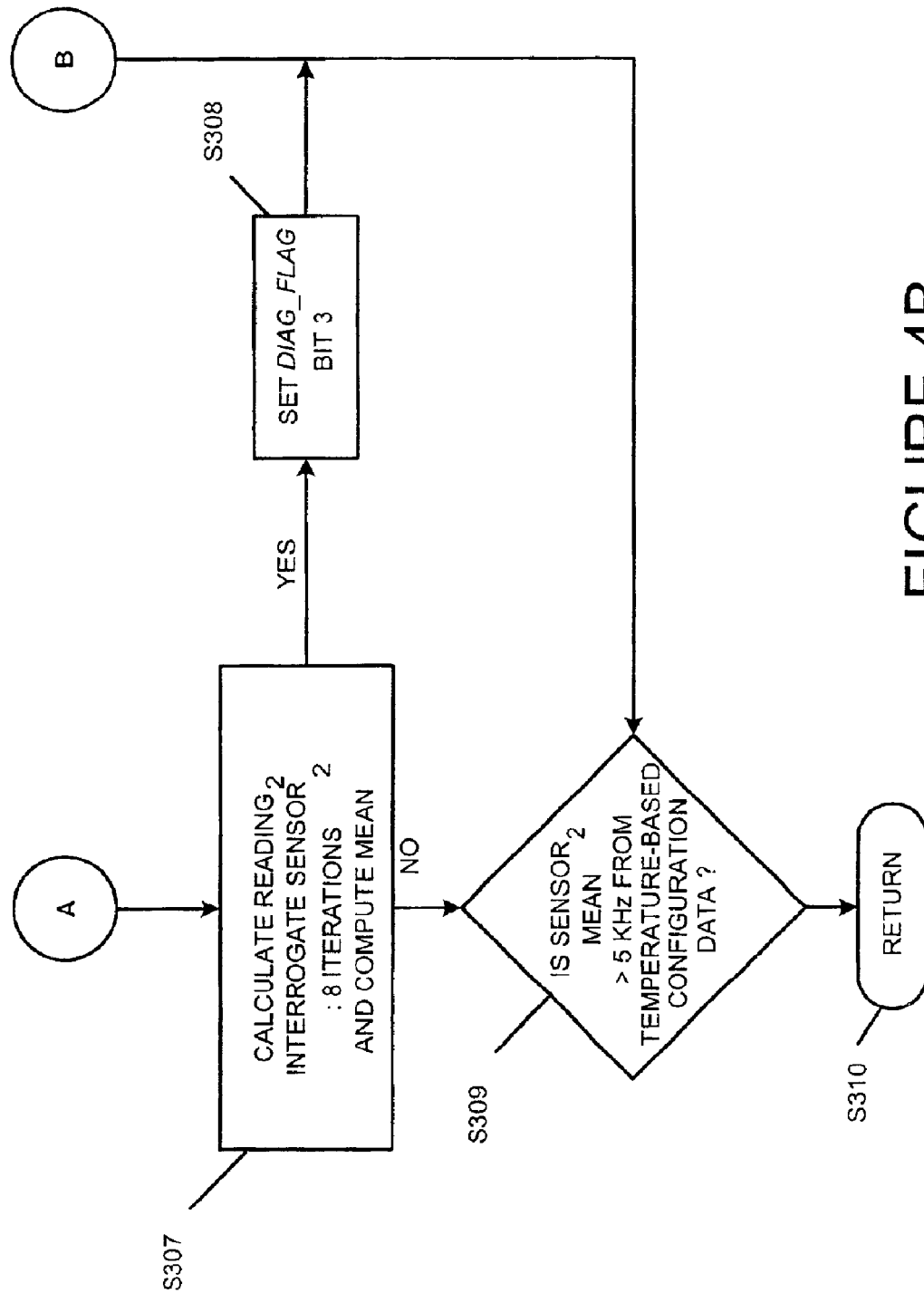

Continuing to FIGS. 4A and 4B, fault conditions detecting particulate accumulation and permanent viscoelastic changes in the gas sensor array 200 overlayer are addressed. Environmental conditions within the process industry are incredibly harsh. Local atmospheres are rich in microscopic particulate and oxidative compounds. Although the design of the chemical detection system 10 reduces exposure and sensitivity to these perturbating factors, elimination is impossible. Any permanent mass loading or oxidation-induced stress on the gas sensor array 200 will cause an irreversible shift, during static flow, in the baseline resonant frequency. Prior to field deployment, an incremental "temperature signature" of fifty gas sensor array 200 baseline readings with one degree Celsius resolution through the operational temperature range are stored in the diagnostic memory 408. The baseline readings are used to compare the present frequencies with the original signature data. Large shifts outside the "signature envelope" at a specific temperature are viewed as fault conditions.

The diagnostic routine is initiated by performing an ambient temperature reading, step S301, with an accuracy of one-degree Celsius. During execution, the sensor interface circuit 402 reports eight sequential sensor readings used to calculate an arithmetic mean and reduce unwanted noise in the baseline resonant frequency of an individual sensor, designated Sensor[1], of the gas sensor array 200, step S302. A conditional statement applies an absolute deviation test on the computed mean, step S304. For example, if the mean baseline resonant frequency is greater than 5 kHz from the signature data, at that present measured temperature, a fault condition is generated, step S305. Fault conditions are reported as previously described. If no fault is generated then execution continues and similar logic applies the test to a second sensor in gas sensor array 200, steps S307–S309. The resolution of the configuration data stored in the diagnostic memory 408 matches the fifty degree Celsius operational span with one degree resolution, thus removing the need to provide an interpolation scheme to calculate temperature-correlated baseline frequencies. Alternatively, greater temperature resolution or an interpolation scheme can be employed. Upon completion of the routine, execution is returned the supervisory diagnostic procedure, step S310.

Figure 5B:
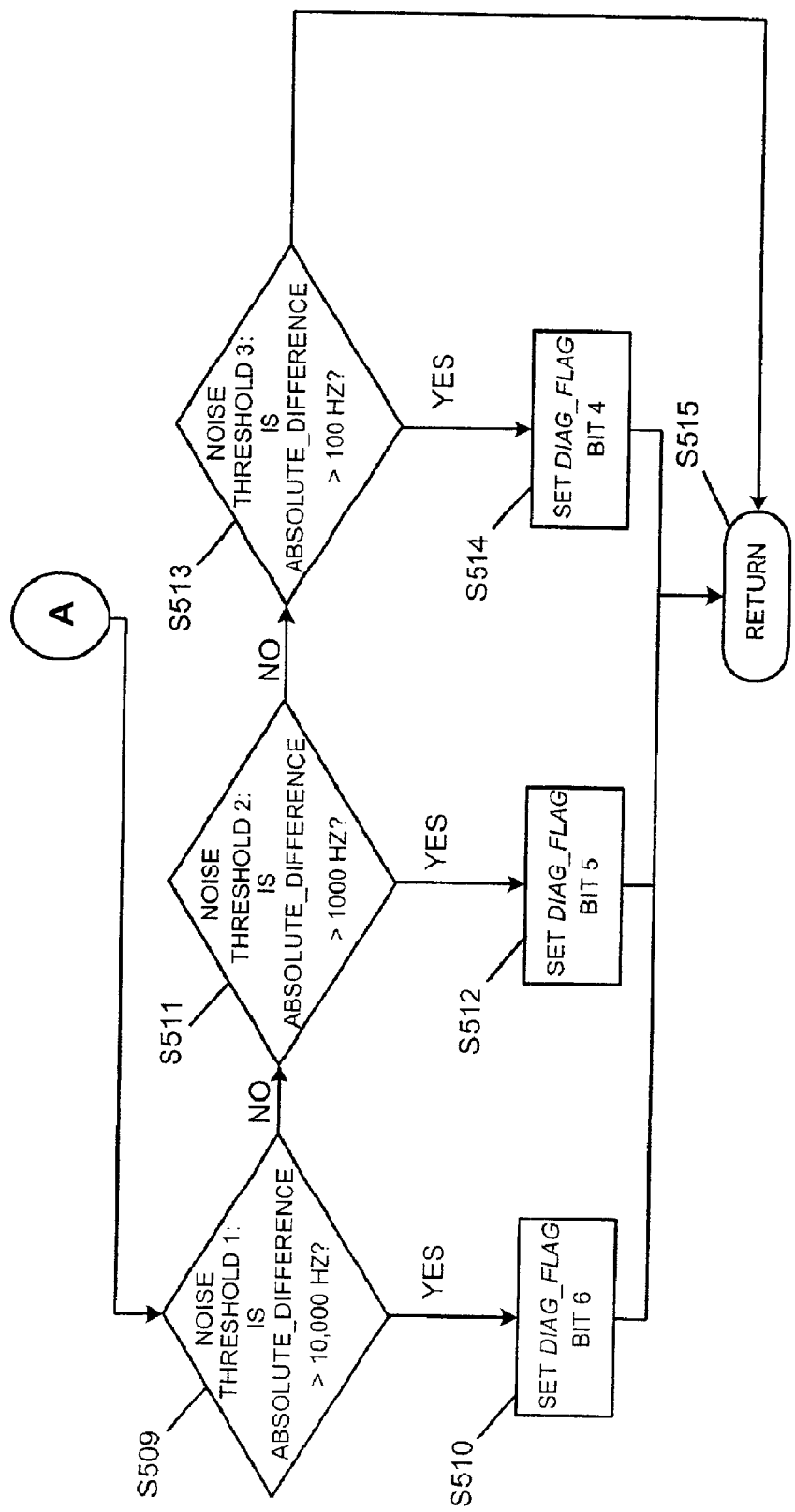

FIGS. 5A and 5B illustrate the noise diagnostic routine for the gas sensor array 200. Noisy sensors are detrimental to system integrity. Poor acoustic coupling of accumulated particulate or overlayer delamination on the gas sensor array 200 will implement itself as erratic deviations in resonant frequency over consecutive measurements. Deviations attributed to frequency skipping (e.g. +5 KHz to +10 KHz), inharmonic tones (e.g. greater than +50 KHz), and broad band noise (e.g. greater than ±100 Hz) are all well known phenomena used in quantifying noise in acoustic wave sensors such as QCMs.

Upon entry of the noise diagnostic routine, two registers, a magnitude register and a sample_count register, in the data memory 409 are initialized prior to execution, step S501. The magnitude register contains the output of the in-line threshold operation. The sample_count register establishes the total number of data samples to be analyzed. The in-line threshold operation checks each of thirty-two consecutive sensor interrogations and retains the maximum value. Acquisition of the gas sensor array 200 data occurs first, step S502. If it is the initial interrogation, the present value is stored as a bias_] value in a memory register of data memory 409, step S504. If it was not the initial interrogation, execution proceeds step S505. An absolute difference is computed between the bias_value and the present value. The absolute difference is calculated since it is the magnitude of the deviation that is of interest, not the arithmetic sign or the direction of the deviation. The absolute difference is compared to the value stored in the magnitude register, step S506. If absolute difference value is larger than value in the magnitude register, the absolute difference value becomes the new maximum value and replaces the previous value stored in magnitude register, steps S506–S508. An iterative loop compares and sorts the thirty-two consecutive reads of the gas sensor array 200. The flowchart diagrammed in FIGS. 5A and 5B depicts the diagnostic logic for a single sensor The same logic can be applied across multiple sensors as dictated by the system design. Furthermore, one skilled in the art can appreciate that the total number of consecutive interrogations may vary greatly without abandoning the spirit of the invention. For example, less iterations may result in an optimistic sensor diagnosis.

Upon exiting the iterative loop, The remaining conditional tests provide quantification of the noise magnitude, steps S509–S514. The results are recorded in another memory register in the data memory 409 and can be used by the main executable to generate an "integrity factor" for the detected emissions. The integrity factor can be used to quantify and report the nature and extent of the fault condition (e.g. frequency skipping, inharmonic tones, or broad band noise). Upon completion of the diagnostic routine, execution is returned to step S110 in the supervisory diagnostic routine, step S515. Fault conditions can be communicated as previously described. This same diagnostic logic is applied prior to and during measurement surveys. When implemented prior to a measurement survey, the failure is indicative of sensor degradation. Application of this routine during a measurement survey can provide operational fault conditions relating to sample retrieval anomalies due to highly variable meteorological conditions (i.e. excessive wind speed).

Referring now to FIGS. 6A and 6B, the issue of diagnosing a saturation limit system fault is embodied. As previously described, emission concentration levels exceeding the gas sensor array 200 saturation limit can do irreparable harm to the sensors, thus degrading chemical detection system 10 performance. The saturation limit potential is detected by measuring the response gradient of the gas sensor array 200. The response gradient is defined by the following equation:

Let:
$\Delta R$=Response Gradient (Hertz per second)
$\Delta F$=Change is Resonant Frequency (Hertz)
$\Delta t$=Change in time (seconds)
Such that, $$\Delta R = \frac{\Delta F}{\Delta t} \text{ (Hertz per second)}$$

A fault condition will be flagged if the response gradient exceeds a threshold value in a specific amount of time. For example, the preferred embodiment establishes this value to be 200 Hertz per second. An arithmetic mean of the magnitude is again calculated to reduce susceptibility to random noise, step S601. The arithmetic mean from the gas sensor array 200 baseline readings is stored in the data memory 409, step S602. The microcontroller 404 opens the exhaust valve 134 and the atmospheric sample valve 130 through the valve driver circuit 407. By opening both valves, a dilution of the emission sample occurs. This dilution protects the gas sensor array 200 from experiencing extremely large emission exposures. It can be appreciated by those skilled in the art that collecting samples individually from the atmospheric and emission ports could also perform saturation limit diagnosis. Continuing, a five second timing loop is executed to allow for the gas sensor array 200 response time without creating an excessive exposure, step S604. Upon completion of the five-second exposure, an average exposure response is calculated. The microcontroller 404 closes the exhaust valve 134 and the atmospheric sample valve 130 to terminate the exposure, steps S605–S606. The response gradient is computed and a conditional test is performed to determine if the threshold has been exceeded, steps S607–S608. If the response gradient exceeded the predetermined threshold value then a fault condition is set and recorded in the diagnostic memory 408. It maybe reported as previously described. If no fault condition is detected, step S609, execution returns operation to the supervisory diagnostic routine. The supervisory diagnostic routine will return execution to the main executable program and the chemical detection system 10 may proceed with a measurement scenario.

Many modifications and variations may be made in the techniques and structures described and illustrated herein without departing from the spirit and scope of the present invention. Accordingly, it should be understood that the methods and apparatus described herein are illustrative only and are not limiting upon the scope of the present invention.

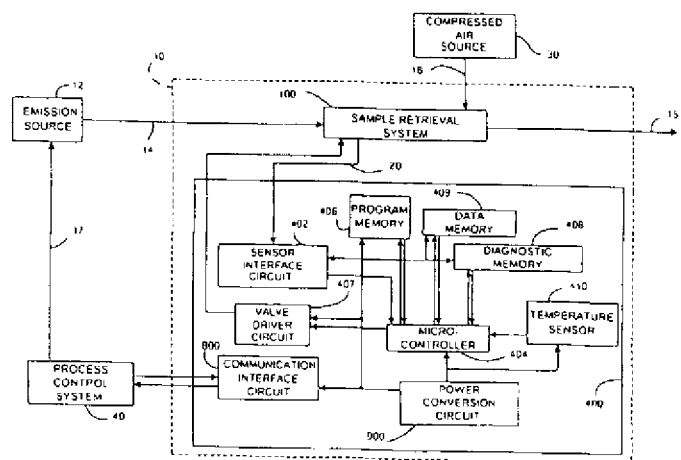

I claim:

1. An apparatus for diagnosing a chemical detection system comprising:
   a sample retrieval device for collecting and detecting emissions, wherein the sample retrieval device includes an accumulator chamber having a sample port for receiving the emission from an emission source, a chemical sensor located within the accumulator chamber for detecting the emission, and an exhaust port for exhausting the detected emission; and
   a control module containing a first operational mode to control the sample retrieval device and a second operational mode to perform a diagnostic routine wherein the diagnostic routine comprises confirming the flow of the emission and a flow of an atmosphere that does not contain a substantial amount of the emission into the chemical detection system, the control module further comprising a diagnostic routine validating the operation of the chemical sensor within the chemical detection system.

2. The apparatus of claim 1, wherein the second operational mode acquires response data from the chemical sensor through controlled exposure to a plurality of emission concentrations.

3. The apparatus of claim 1, wherein the diagnostic routine includes measuring the absolute frequency shift of the chemical sensor.

4. The apparatus of claim 1, wherein the diagnostic routine includes acquiring response data from the chemical sensor and quantifying the noise within the response data.

5. The apparatus of claim 1, wherein the diagnostic routine includes performing controlled exposures on the chemical sensor to determine the presence of an emission concentration capable of permanently changing the chemical sensor.

6. A method for verifying the operation of a chemical detection system, the method comprising the steps of:
   performing diagnostic routines on the chemical detection system, the diagnostic routines comprising controlling the exposure of a chemical sensor and taking measurements of surrounding environmental conditions;
   measuring the response of a chemical sensor to the controlled exposure and the surrounding environmental conditions;
   storing response data in a memory device; and
   generating diagnostic data from the response data wherein the diagnostic routines includes confirming the flow of an emission and a flow of an atmosphere that does not contain a substantial amount of an emission into the chemical detection system, the diagnostic routine further validating the operation of the chemical sensor within the chemical detection system.

7. The method of claim 6, wherein the diagnostic routines include computing a transient flow sensitivity response by calculating the absolute value of the arithmetic difference of a first average chemical sensor response and a second average chemical sensor response, the first average chemical sensor response computed under static flow conditions without exposure to an emission, the second average chemical sensor response computed under dynamic flow conditions without exposure to an emission.

8. The method of claim 6, wherein the diagnostic routine includes quantifying the chemical sensor saturation potential.

9. The method of claim 8, wherein the diagnostic routine further includes computing a sensor response gradient, the sensor response gradient being calculated by a ratio of a sensor response threshold arithmetically divided by a predetermined time interval, wherein the sensor response threshold is determined by performing the absolute value of the arithmetic difference of a first average chemical sensor response and a second average chemical sensor response, the first average chemical sensor response computed under static flow conditions without exposure to an emission, the second average chemical sensor response computed value under static flow conditions with exposure to an emission.

10. The method of claim 6, wherein measuring the response of the chemical sensor to the controlled exposure is comprised of quantifying chemical sensor noise.

11. The method of claim 10, wherein quantifying chemical sensor noise is accomplished by comparing an absolute arithmetic difference to at least one noise threshold value, the noise threshold value providing a graduated fault condition.

12. The method of claim 11, wherein comparing the absolute arithmetic difference is performed by computing calculating the absolute value of the arithmetic difference between an average chemical sensor response and the noise threshold value stored in memory, the average chemical sensor response computed under static flow conditions without exposure to an emission.

13. A method for verifying the operation of a chemical detection system, the method comprising the steps of:
   performing diagnostic routines on the chemical detection system, the diagnostic routines comprising controlling the exposure of a chemical sensor and taking measurements of surrounding environmental conditions;
   measuring the response of a chemical sensor to the controlled exposure and the surrounding environmental conditions;
   storing response data in a memory device; and
   generating diagnostic data from the response data wherein the diagnostic routines include confirming the flow of an emission and confirming the flow of an atmosphere that does not contain a substantial amount of an emission through the chemical detection system, the diagnostic routines further including computing a transient flow sensitivity response by calculating the absolute value of the arithmetic difference of a first average chemical sensor response and a second average chemical sensor response, the first average chemical sensor response computed under static flow conditions without substantial exposure to an emission, the second average chemical sensor response computed under dynamic flow conditions without substantial exposure to an emission.

14. A method for verifying the operation of a chemical detection system, the method comprising the steps of:

performing diagnostic routines on the chemical detection system, the diagnostic routines comprising controlling the exposure of a chemical sensor and taking measurements of surrounding environmental conditions;

measuring the response of a chemical sensor to the controlled exposure and the surrounding environmental conditions;

storing response data in a memory device; and generating diagnostic data from the response data wherein the diagnostic routine includes quantifying the chemical sensor saturation potential, the diagnostic routine further including computing a sensor response gradient, the sensor response gradient being calculated by a ratio of a sensor response threshold arithmetically divided by a predetermined time interval, wherein the sensor response threshold is determined by performing the absolute value of the arithmetic difference of a first average chemical sensor response and a second average chemical sensor response, the first average chemical sensor response computed under static flow conditions without substantial exposure to an emission, the second average chemical sensor response computed value under static flow conditions with exposure to an emission.

15. A method for verifying the operation of a chemical sensor, the method comprising the steps of:

performing diagnostic routines on the chemical sensor, the diagnostic routines comprising controlling the exposure of the chemical sensor to emissions and taking measurements of surrounding environmental conditions;

measuring the response of a chemical sensor to the controlled exposure;

storing response data in a memory device; and generating diagnostic data from the response data wherein measuring the response of the chemical sensor to the controlled exposure is comprised of measuring an ambient temperature and an absolute frequency shift of the chemical sensor wherein the absolute frequency shift measurement is performed by computing the arithmetic difference between an average chemical sensor response and a configuration sensor response stored in the memory device, the average chemical sensor response computed under static flow conditions without substantial exposure to the emission, wherein the configuration sensor response value is computed under static flow conditions prior to exposure to the emission.

16. A method for determining fault conditions of a chemical sensor, the method comprising the steps of:

performing diagnostic routines on the chemical sensor, the diagnostic routines comprising controlling the exposure of the chemical sensor to emissions and taking measurements of surrounding environmental conditions;

measuring the response of a chemical sensor to the controlled exposure such that measuring the response of the chemical sensor is comprised of measuring an ambient temperature and an absolute frequency shift of the chemical sensor wherein the absolute frequency shift measurement is performed by computing the arithmetic difference between an average chemical sensor response and a configuration sensor response stored in the memory device, the average chemical sensor response being computed under static flow conditions without exposure to the emission and the configuration sensor response value being computed under static flow conditions prior to exposure to the emission;

storing response data in a memory device; and generating diagnostic data from the response data.

17. A method for determining fault conditions of a chemical sensor, the method comprising the steps of:

performing diagnostic routines on the chemical sensor, the diagnostic routines comprising controlling the exposure of the chemical sensor to emissions and taking measurements of surrounding environmental conditions;

measuring the response of a chemical sensor to the controlled exposure wherein measuring the response of the chemical sensor is comprised of quantifying chemical sensor noise by comparing an absolute arithmetic difference to at least one noise threshold value wherein the noise threshold value provides a graduated fault condition and the absolute arithmetic difference is performed by calculating the absolute value of the arithmetic difference between an average chemical sensor response and the noise threshold value stored in memory, the average chemical sensor response computed under static flow conditions without exposure to an emission and the configuration sensor response being computed value under static flow conditions prior to exposure to an emission;

storing response data in a memory device; and generating diagnostic data from the response data.

* * * * *

UNITED STATES PATENT AND TRADEMARK OFFICE
CERTIFICATE OF CORRECTION

PATENT NO. : 6,879,936 B2  Page 1 of 1
APPLICATION NO. : 10/042979
DATED : April 12, 2005
INVENTOR(S) : John P. Dilger It is certified that error appears in the above-identified patent and that said Letters Patent is hereby corrected as shown below:

At Column 3, line 62, please delete "International Inc." and insert --International, Inc.--
At Column 6, line 31, please delete "a" immediately after "for"
At Column 6, line 57, please delete "be" immediately after "will"
At Column 7, line 10, please delete "induces" and insert --induce--
At Column 8, line 17, please delete "of" immediately after "condition"
At Column 9, line 24, please delete "Sensor[1]" and insert --Sensor--
At Column 9, line 62, please delete "bias_] value" and insert --bias_value--
At Column 10. line 6, please insert --the-- immediately before "magnitude"
At Column 10, line 9, please delete "sensor" and insert --sensor.--
At Column 10, line 17, please delete "loop, The" and insert --loop, the--

In Claim 7, Column 12, line 3, please delete "includes" and insert --include--
In Claim 12, at Column 12, line 43-44, please delete "computing"

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,879,936 B2 | |
| APPLICATION NO. | : 10/042979 | |
| DATED | : April 12, 2005 | |
| INVENTOR(S) | : John P. Dilger | |

It is certified that error appears in the above-identified patent and that said Letters Patent is hereby corrected as shown below:

The title page showing the illustrative figure should be deleted to be replaced with the attached title page.

In the Drawings, Figs. 1A, 1B, 1C, 2A, 2B, 3A, 3B, 4B, 5B, 6A and 6B should be replaced with the corrected Figs. 1A, 1B, 1C, 2A, 2B, 3A, 3B, 4B, 5B, 6A and 6B as shown on the attached pages.

At column 4, line 64, "the ejector 114" should be --the ejector 140--;
At column 7, line 44, "proscribed" should be --prescribed--;
At column 10, line 62, "atmospheric sample valve 130" should be --emission sample valve 130--;
At column 11, line 7, "atmospheric sample valve 130" should be --emission sample valve 130--;
At column 11, line 13, "diagnostic memory 408." should be --diagnostic memory 408, step S609.--;
At column 11, line 14, "detected, step S609," should be --detected,--.

In the Claims:

In Claim 6, at column 11, line 65, "measuring the response of a chemical sensor" should be
--measuring the response of the chemical sensor--;
In Claim 6, at column 12, line 3, "diagnostic routines includes confirming" should be
--diagnostic routines include confirming--;
In Claim 6, at column 12, line 5, "substantial amount of an emission" should be --substantial amount of the emission--;
In Claim 6, at column 12, lines 6-7, "the diagnostic routine further validating" should be
--the diagnostic routines further validating--;
In Claim 7, at column 12, lines 14-15, "without exposure to an emission," should be --without exposure to the emission--;
In Claim 7, at column 12, line 17, "without exposure to an emission," should be --without exposure to the emission--;
In Claim 8, at column 12, lines 18-19, "diagnostic routine includes quantifying" should be
--diagnostic routines include quantifying--;

Signed and Sealed this
Fourteenth Day of August, 2012

David J. Kappos
*Director of the United States Patent and Trademark Office*

CERTIFICATE OF CORRECTION (continued)
U.S. Pat. No. 6,879,936 B2

In Claim 9, at column 12, lines 21-22, "diagnostic routine further includes computing" should be --diagnostic routines further include computing--;

In Claim 9, at column 12, line 30, "without exposure to an emission" should be --without exposure to the emission--;

In Claim 9, at column 12, lines 31-32, "computed value under static flow conditions with exposure to an emission." should be --computed under static flow conditions with exposure to the emission.--;

In Claim 11, at column 12, lines 36-37, "wherein quantifying chemical sensor" should be --wherein quantifying the chemical sensor--;

In Claim 12, at column 12, line 45, "value stored in memory" should be --value stored in the memory device--;

In Claim 12, at column 12, lines 46-47, "conditions without exposure to an emission." should be --conditions without exposure to the emission.--;

In Claim 13, at column 12, line 54, "response of a chemical sensor" should be --response of the chemical sensor--;

In Claim 13, at column 13, line 3, "substantial exposure to an emission," should be --substantial exposure to the emission,--;

In Claim 13, at column 13, lines 5-6, "substantial exposure to an emission." should be --substantial exposure to the emission.--;

In Claim 14, at column 13, line 13, "response of a chemical sensor" should be --response of the chemical sensor--;

In Claim 14, at column 13, line 18, "diagnostic routine includes quantifying" should be --diagnostic routines include quantifying--;

In Claim 14, at column 13, lines 19-20, "diagnostic routine further including" should be --diagnostic routines further including--;

In Claim 14, at column 13, lines 30-32, "computed value under static flow conditions with exposure to an emission." should be --computed under static flow conditions with exposure to the emission--;

In Claim 15, at column 13, line 41, "response of a chemical sensor" should be --response of the chemical sensor--;

In Claim 15, at column 14, lines 1-4, "to the emission, wherein the configuration sensor response value is computed under static flow conditions prior to exposure to the emission." should be --to the emissions, wherein the configuration sensor response is computed under static flow conditions prior to exposure to the emissions.--;

In Claim 16, at column 14, line 12, "response of a chemical sensor" should be --response of the chemical sensor--;

In Claim 16, at column 14, line 20, "stored in the memory device," should be --stored in a memory device,--;

In Claim 16, at column 14, line 22, "exposure to the emission and" should be --exposure to the emissions and--;

In Claim 16, at column 14, line 24, "exposure to the emission;" should be --exposure to the emissions;--;

In Claim 16, at column 14, line 25, "storing response data in a memory device;" should be --storing response data in the memory device;--;

In Claim 17, at column 14, line 35, "response of a chemical sensor" should be --response of the chemical sensor--;

In Claim 17, at column 14, lines 44-45, "value stored in memory," should be --value stored in a memory device,--;

In Claim 17, at column 14, lines 46-47, "without exposure to an emission" should be --without exposure to the emissions--;

In Claim 17, at column 14, lines 48-49, "computed value under static flow conditions prior to exposure to an emission" should be --computed under static flow conditions prior to exposure to the emission--;

In Claim 17, at column 14, line 50, "storing response data in a memory device;" should be --storing response data in the memory device;--.

(12) United States Patent
Dilger

(10) Patent No.: US 6,879,936 B2
(45) Date of Patent: Apr. 12, 2005

(54) DIAGNOSTIC APPARATUS AND METHODS FOR A CHEMICAL DETECTION SYSTEM

(75) Inventor: John P. Dilger, Marshalltown, IA (US)

(73) Assignee: Fisher Controls International LLC, St. Louis, MO (US)

(*) Notice: Subject to any disclaimer, the term of this patent is extended or adjusted under 35 U.S.C. 154(b) by 379 days.

(21) Appl. No.: 10/042,979

(22) Filed: Jan. 9, 2002

(65) Prior Publication Data

US 2003/0127340 A1 Jul. 10, 2003

(51) Int. Cl.[7] .................................................. G01N 1/00
(52) U.S. Cl. ...................... 702/183; 702/22; 702/23; 702/30; 702/31; 702/32; 702/104; 702/127
(58) Field of Search .................... 702/22–27, 30–32, 702/50, 51, 85, 90, 91, 104, 127–129, 183, 185; 73/23.31, 169; 340/632, 634, 605; 700/272; 422/58; 205/775

(56) References Cited

U.S. PATENT DOCUMENTS

| | | | | |
|---|---|---|---|---|
| 4,461,167 A | * | 7/1984 | Kent et al. | 73/29.02 |
| 4,627,269 A | * | 12/1986 | Forster et al. | 73/31.06 |
| 4,703,646 A | * | 11/1987 | Muller et al. | 73/24.01 |
| 4,726,225 A | * | 2/1988 | Brace et al. | 73/204.23 |
| 5,410,495 A | | 4/1995 | Ramamurthi | 702/100 |
| 5,451,923 A | | 9/1995 | Scherger et al. | 340/310.06 |
| 5,487,312 A | | 1/1996 | Kahl et al. | 73/863.01 |
| 5,541,851 A | * | 7/1996 | Sato et al. | 700/266 |
| 5,569,838 A | * | 10/1996 | Broedel et al. | 73/23.31 |
| 5,733,436 A | | 3/1998 | Demisch et al. | 205/775 |
| 5,814,524 A | * | 9/1998 | Walt et al. | 436/518 |
| 6,029,506 A | * | 2/2000 | Dilger | 73/46 |
| 6,174,289 B1 | | 1/2001 | Binder | 600/532 |
| 6,200,443 B1 | | 3/2001 | Shen et al. | 204/401 |
| 6,222,366 B1 | | 4/2001 | Dilger | 324/319 |
| 6,272,938 B1 | * | 8/2001 | Baghel et al. | 73/863.23 |
| 6,300,638 B1 | * | 10/2001 | Groger et al. | 250/458.1 |
| 6,345,234 B1 | * | 2/2002 | Dilger et al. | 702/24 |
| 6,455,319 B1 | * | 9/2002 | Lewis et al. | 436/151 |
| 6,532,793 B1 | * | 3/2003 | Palocz-Andresen | 73/23.31 |
| 6,539,311 B1 | * | 3/2003 | Berger | 702/23 |
| 6,647,343 B1 | * | 11/2003 | Guthrie et al. | 702/30 |
| 2003/0052083 A1 | * | 3/2003 | Kim et al. | 216/59 |

FOREIGN PATENT DOCUMENTS

| | | | |
|---|---|---|---|
| GB | 841563 a | * | 5/1998 |
| WO | WO 99/12471 | | 3/1999 |
| WO | WO 00/67634 | | 11/2000 |

OTHER PUBLICATIONS

International Preliminary Examination Report for PCT/US02/36924, mailed Apr. 14, 2004.
Written Opinion for PCT/US02/36924, mailed Dec. 8, 2003.
International Search Report for PCT/US02/36924, issued Apr. 16, 2003.

* cited by examiner

Primary Examiner—Carol S Tsai
(74) Attorney, Agent, or Firm—Marshall, Gerstein & Borun LLP

(57) ABSTRACT

A chemical detection system performs controlled exposures to diagnose the pneumatic components and chemical sensors prior to measuring a chemical emission. A control module provides the system control and data processing to perform the diagnosis. The control module manipulates an emission sample retrieval system to provide precise exposure during the diagnostic routines. A sensor interface circuit interrogates the chemical sensors and stores the data for analysis. The chemical sensor exhibits predictable changes in response during predetermined exposure scenarios. By utilizing numerous time domain signal processing techniques, both system and sensor level fault conditions are determined.

17 Claims, 14 Drawing Sheets